US012616523B2

(12) United States Patent
Caldera et al.

(10) Patent No.: US 12,616,523 B2
(45) Date of Patent: May 5, 2026

(54) SURGEON PREFERENCES AND WARNING VISUALIZATIONS FOR IMPLANT PLANNING

(71) Applicant: MAKO Surgical Corp., Weston, FL (US)

(72) Inventors: Lizeth Joann Caldera, Miami, FL (US); Jason Otto, Sioux Falls, SD (US); Morgan Fitzgerald, Plantation, FL (US); Milan Ikits, Weston, FL (US); Ajeet Singh Yadav, Lucknow (IN); Arun Shreedhar, Bengaluru (IN); Kevin Froster, Marlboro, NJ (US); Christine Perrone, Warwick, NY (US); Ta-Cheng Chang, Weston, FL (US)

(73) Assignee: MAKO SURGICAL CORP., Weston, FL (US)

( * ) Notice: Subject to any disclaimer, the term of this patent is extended or adjusted under 35 U.S.C. 154(b) by 1055 days.

(21) Appl. No.: 17/514,705

(22) Filed: Oct. 29, 2021

(65) Prior Publication Data

US 2022/0183757 A1 Jun. 16, 2022

Related U.S. Application Data

(60) Provisional application No. 63/226,858, filed on Jul. 29, 2021, provisional application No. 63/177,034, (Continued)

(51) Int. Cl.
| | |
|---|---|
| *A61B 34/20* | (2016.01) |
| *A61B 17/02* | (2006.01) |

(Continued)

(52) U.S. Cl.
CPC ............. *A61B 34/20* (2016.02); *A61B 34/10* (2016.02); *A61B 34/25* (2016.02); *A61B 34/30* (2016.02);

(Continued)

(58) Field of Classification Search
CPC ......... A61B 34/20; A61B 34/10; A61B 34/25; A61B 34/30; A61B 90/06; A61B 90/39;
(Continued)

(56) References Cited

U.S. PATENT DOCUMENTS

| | | |
|---|---|---|
| 4,559,936 A | 12/1985 | Hill |
| 5,078,140 A | 1/1992 | Kwoh |

(Continued)

FOREIGN PATENT DOCUMENTS

| | | | | |
|---|---|---|---|---|
| AU | 2049915/19 | 8/2019 | | |
| CN | 111739644 A | * 10/2020 | ............. | G06F 18/22 |

(Continued)

OTHER PUBLICATIONS

US 9,445,923 B2, 09/2016, Arthromeda (withdrawn)
(Continued)

*Primary Examiner* — Rehana Perveen
*Assistant Examiner* — John P Hocker
(74) *Attorney, Agent, or Firm* — Foley & Lardner LLP

(57) ABSTRACT

A method for controlling a robotic system to facilitate a joint arthroplasty procedure includes generating a graphical user interface comprising a visualization of an implant plan and an indication of a user-defined value for an implant planning parameter, and comparing the user-defined value for the implant planning parameter to the range. The method includes providing a marking at the indication of the user-defined value on the graphical user interface and receiving an update to the implant plan, wherein the update to the implant plan causes a change in the user-defined value. The method further includes determining that the change in the user-defined value moved the user-defined value to within the selected preferred range.

20 Claims, 19 Drawing Sheets

Related U.S. Application Data filed on Apr. 20, 2021, provisional application No. 63/125,468, filed on Dec. 15, 2020.

(51) Int. Cl.

| | |
|---|---|
| *A61B 34/00* | (2016.01) |
| *A61B 34/10* | (2016.01) |
| *A61B 34/30* | (2016.01) |
| *A61B 34/35* | (2016.01) |
| *A61B 90/00* | (2016.01) |
| *A61F 2/46* | (2006.01) |

(52) U.S. Cl.
CPC .............. *A61B 90/06* (2016.02); *A61B 90/39* (2016.02); *A61B 2017/0268* (2013.01); *A61B 2034/102* (2016.02); *A61B 2034/104* (2016.02); *A61B 2034/105* (2016.02); *A61B 2034/2068* (2016.02); *A61B 2034/252* (2016.02); *A61B 34/35* (2016.02); *A61B 2090/064* (2016.02); *A61B 2090/067* (2016.02); *A61B 2090/3916* (2016.02); *A61F 2/46* (2013.01)

(58) Field of Classification Search
CPC ............ A61B 34/35; A61B 2017/0268; A61B 2034/102; A61B 2034/104; A61B 2034/105; A61B 2034/2068; A61B 2034/252; A61B 2090/064; A61B 2090/067; A61B 2090/3916; A61B 2034/254; A61B 2034/2055; A61B 2034/2059; A61B 17/025; A61F 2/46

See application file for complete search history.

(56) References Cited

U.S. PATENT DOCUMENTS

| | | | |
|---|---|---|---|
| 5,413,573 A | 5/1995 | Koivukangas | |
| 5,540,696 A | 7/1996 | Booth et al. | |
| 5,630,431 A | 5/1997 | Taylor | |
| 5,682,886 A | 11/1997 | Delp et al. | |
| 5,800,438 A | 9/1998 | Tuke et al. | |
| 5,824,085 A | 10/1998 | Sahay et al. | |
| 6,328,752 B1 | 12/2001 | Sjostrom et al. | |
| 6,595,997 B2 | 7/2003 | Axelson et al. | |
| 6,685,711 B2 | 2/2004 | Axelson et al. | |
| 6,758,850 B2 | 7/2004 | Smith et al. | |
| 6,827,723 B2 | 12/2004 | Carson | |
| 6,859,661 B2 | 2/2005 | Tuke | |
| 7,008,362 B2 | 3/2006 | Fitzgibbon | |
| 7,412,897 B2 | 8/2008 | Crottet et al. | |
| 7,510,557 B1 | 3/2009 | Bonutti | |
| 7,547,307 B2 | 6/2009 | Carson et al. | |
| 7,591,821 B2 | 9/2009 | Kelman | |
| 7,607,440 B2 | 10/2009 | Coste-Maniere et al. | |
| 7,618,421 B2 | 11/2009 | Axelson et al. | |
| 7,634,306 B2 | 12/2009 | Sarin et al. | |
| 7,670,345 B2 | 3/2010 | Plassky et al. | |
| 7,696,899 B2 | 4/2010 | Immerz et al. | |
| 7,794,467 B2 | 9/2010 | McGinley et al. | |
| 7,831,295 B2 | 11/2010 | Friedrich et al. | |
| 7,927,336 B2 | 4/2011 | Rasmussen | |
| 7,931,655 B2 | 4/2011 | Axelson et al. | |
| 7,945,310 B2 | 5/2011 | Gattani et al. | |
| 7,963,913 B2 | 6/2011 | Devengenzo et al. | |
| 8,007,448 B2 | 8/2011 | Moctezuma De La Barrera | |
| 8,010,180 B2 | 8/2011 | Quaid et al. | |
| 8,038,683 B2 | 10/2011 | Couture et al. | |
| 8,075,317 B2 | 12/2011 | Youngblood | |
| 8,078,440 B2 | 12/2011 | Otto et al. | |
| 8,096,997 B2 | 1/2012 | Plaskos et al. | |
| 8,109,942 B2 | 2/2012 | Carson | |
| 8,116,847 B2 | 2/2012 | Gattani et al. | |
| 8,126,533 B2 | 2/2012 | Lavallee | |
| 8,160,345 B2 | 4/2012 | Pavlovskaia et al. | |
| 8,170,888 B2 | 5/2012 | Silverman | |
| 8,172,775 B2 | 5/2012 | Warkentine et al. | |
| 8,197,549 B2 | 6/2012 | Amirouche et al. | |
| 8,257,360 B2 | 9/2012 | Richard et al. | |
| 8,265,790 B2 | 9/2012 | Amiot et al. | |
| 8,265,949 B2 | 9/2012 | Haddad | |
| 8,277,455 B2 | 10/2012 | Couture et al. | |
| 8,337,508 B2 | 12/2012 | Lavallee et al. | |
| 8,357,111 B2 | 1/2013 | Caillouette et al. | |
| 8,377,129 B2 | 2/2013 | Fitz et al. | |
| 8,382,765 B2 | 2/2013 | Axelson et al. | |
| 8,386,077 B2 | 2/2013 | Birkenbach et al. | |
| 8,480,679 B2 | 7/2013 | Park et al. | |
| 8,483,469 B2 | 7/2013 | Pavlovskaia et al. | |
| 8,521,252 B2 | 8/2013 | Diez | |
| 8,545,509 B2 | 10/2013 | Park et al. | |
| 8,548,559 B2 | 10/2013 | Hodgson et al. | |
| 8,551,023 B2 | 10/2013 | Sherman et al. | |
| 8,551,099 B2 | 10/2013 | Lang et al. | |
| 8,626,267 B2 | 1/2014 | Lavallee | |
| 8,641,726 B2 | 2/2014 | Bonutti | |
| 8,682,052 B2 | 3/2014 | Fitz et al. | |
| 8,707,963 B2 | 4/2014 | Davis et al. | |
| 8,715,291 B2 | 5/2014 | Park et al. | |
| 8,721,568 B2 | 5/2014 | Rock et al. | |
| 8,777,875 B2 | 7/2014 | Park | |
| 8,801,719 B2 | 8/2014 | Park et al. | |
| 8,801,720 B2 | 8/2014 | Park et al. | |
| 8,832,019 B2 | 9/2014 | Gao | |
| 8,834,490 B2 | 9/2014 | Bonutti | |
| 8,845,645 B2 | 9/2014 | Wilkinson et al. | |
| 8,861,818 B2 | 10/2014 | Ito et al. | |
| 8,880,152 B2 | 11/2014 | Lavallee | |
| 8,885,904 B2 | 11/2014 | Darrow et al. | |
| 8,938,282 B2 | 1/2015 | Daon et al. | |
| 8,951,260 B2 | 2/2015 | Lang et al. | |
| 8,956,355 B2 | 2/2015 | Edwards et al. | |
| 8,965,483 B2 | 2/2015 | Couture et al. | |
| 8,974,468 B2 | 3/2015 | Borja | |
| 8,979,859 B2 | 3/2015 | Leparmentier et al. | |
| 9,002,426 B2 | 4/2015 | Quaid et al. | |
| 9,101,394 B2 | 8/2015 | Arata et al. | |
| 9,119,722 B1 | 9/2015 | Kusuma | |
| 9,125,669 B2 | 9/2015 | Ranawat et al. | |
| 9,167,989 B2 | 10/2015 | Odermatt et al. | |
| 9,168,153 B2 | 10/2015 | Bettenga | |
| 9,173,716 B2 | 11/2015 | Kasodekar et al. | |
| 9,186,292 B2 | 11/2015 | Besendorfer | |
| 9,220,510 B2 | 12/2015 | Cheal et al. | |
| 9,237,951 B1 | 1/2016 | Hakki | |
| 9,241,801 B1 | 1/2016 | Parry et al. | |
| 9,247,998 B2 | 2/2016 | Hladio et al. | |
| 9,248,001 B2 | 2/2016 | Colombet et al. | |
| 9,259,290 B2 | 2/2016 | Jenkins et al. | |
| 9,262,802 B2 | 2/2016 | Aghazadeh | |
| 9,265,447 B2 | 2/2016 | Stein et al. | |
| 9,271,756 B2 | 3/2016 | Van Der Walt et al. | |
| 9,277,968 B2 | 3/2016 | Min et al. | |
| 9,286,355 B2 | 3/2016 | De Guise et al. | |
| 9,289,264 B2 | 3/2016 | Iorgulescu et al. | |
| 9,301,812 B2 | 4/2016 | Kehres et al. | |
| 9,332,987 B2 | 5/2016 | Leimbach et al. | |
| 9,406,134 B2 | 8/2016 | Klingenbeck-Regn | |
| 9,433,425 B2 | 9/2016 | Wilkinson | |
| 9,439,656 B2 | 9/2016 | Chana et al. | |
| 9,517,000 B2 | 12/2016 | Donhowe et al. | |
| 9,532,788 B2 | 1/2017 | Jordan et al. | |
| 9,532,838 B2 | 1/2017 | Coste-Maniere et al. | |
| 9,549,742 B2 | 1/2017 | Berend et al. | |
| 9,549,782 B2 | 1/2017 | Park et al. | |
| 9,554,953 B2 | 1/2017 | Dirauf et al. | |
| 9,561,082 B2 | 2/2017 | Yen et al. | |
| 9,572,682 B2 | 2/2017 | Aghazadeh | |
| 9,585,725 B2 | 3/2017 | Bonutti | |
| 9,585,768 B2 | 3/2017 | Sherman et al. | |
| 9,592,133 B2 | 3/2017 | Toler et al. | |
| 9,597,096 B2 | 3/2017 | Aghazadeh | |
| 9,610,086 B2 | 4/2017 | Park et al. | |

(56) References Cited

U.S. PATENT DOCUMENTS

| | | | |
|---|---|---|---|
| 9,610,134 B2 | 4/2017 | Kubiak et al. |
| 9,639,156 B2 | 5/2017 | Iorgulescu et al. |
| 9,684,768 B2 | 6/2017 | Lavallee et al. |
| 9,700,292 B2 | 7/2017 | Nawana et al. |
| 9,724,165 B2 | 8/2017 | Arata et al. |
| 9,737,311 B2 | 8/2017 | Lavallee et al. |
| 9,737,369 B2 | 8/2017 | Burger et al. |
| 9,763,683 B2 | 9/2017 | Bonutti |
| 9,763,746 B2 | 9/2017 | Deichmann et al. |
| 9,782,226 B2 | 10/2017 | Park et al. |
| 9,782,229 B2 | 10/2017 | Crawford et al. |
| 9,808,356 B2 | 11/2017 | Haight et al. |
| 9,848,896 B2 | 12/2017 | Emslie et al. |
| 9,861,446 B2 | 1/2018 | Lang |
| 9,888,931 B2 | 2/2018 | Bake |
| 9,901,404 B2 | 2/2018 | Park et al. |
| 9,901,463 B2 | 2/2018 | Mahfouz |
| 9,911,187 B2 | 3/2018 | Steinle et al. |
| 9,913,691 B2 | 3/2018 | Brooks |
| 9,913,692 B2 | 3/2018 | Arata et al. |
| 9,916,421 B2 | 3/2018 | Vorhis et al. |
| 9,987,092 B2 | 6/2018 | Hladio et al. |
| 10,010,377 B2 | 7/2018 | Iorgulescu et al. |
| 10,052,164 B2 | 8/2018 | Overmyer |
| 10,070,931 B2 | 9/2018 | Itkowitz et al. |
| 10,070,973 B2 | 9/2018 | Sherman et al. |
| 10,071,488 B2 | 9/2018 | Robinson et al. |
| 10,076,344 B2 | 9/2018 | Toler |
| 10,080,616 B2 | 9/2018 | Wilkinson et al. |
| 10,092,361 B2 | 10/2018 | Ferro et al. |
| 10,102,309 B2 | 10/2018 | Mckinnon et al. |
| 10,117,658 B2 | 11/2018 | Talbot |
| 10,130,375 B2 | 11/2018 | Yager et al. |
| 10,136,950 B2 | 11/2018 | Schoenefeld |
| 10,136,952 B2 | 11/2018 | Couture et al. |
| 10,172,687 B2 | 1/2019 | Garbus et al. |
| 10,194,991 B2 | 2/2019 | Bonny et al. |
| 10,201,320 B2 | 2/2019 | Saget et al. |
| 10,206,714 B2 | 2/2019 | Van Der Walt et al. |
| 10,206,792 B2 | 2/2019 | Sherman et al. |
| 10,226,261 B2 | 3/2019 | Park et al. |
| 10,226,306 B2 | 3/2019 | Itkowitz et al. |
| 10,231,739 B1 | 3/2019 | Bonutti |
| 10,231,786 B2 | 3/2019 | Ferro et al. |
| 10,238,454 B2 | 3/2019 | Boettner et al. |
| 10,271,954 B2 | 4/2019 | Roach et al. |
| 10,272,569 B2 | 4/2019 | Swarup et al. |
| 10,278,777 B1 | 5/2019 | Lang |
| 10,285,683 B2 | 5/2019 | Plaskos et al. |
| 10,307,269 B2 | 6/2019 | Miller |
| 10,368,947 B2 | 8/2019 | Lang |
| 10,416,624 B2 | 9/2019 | Bly et al. |
| 10,420,611 B2 | 9/2019 | Jaramaz et al. |
| 10,426,556 B2 | 10/2019 | Miga et al. |
| 10,441,366 B2 | 10/2019 | Tabandeh et al. |
| 10,441,438 B1 | 10/2019 | Rahman et al. |
| 10,452,238 B2 | 10/2019 | Nikou et al. |
| 10,456,075 B2 | 10/2019 | Auchinleck et al. |
| 10,456,166 B2 | 10/2019 | Cooper et al. |
| 10,463,242 B2 | 11/2019 | Kesten et al. |
| 10,470,838 B2 | 11/2019 | Epstein et al. |
| 10,492,693 B2 | 12/2019 | Irisawa |
| 10,492,798 B2 | 12/2019 | Metzger |
| 10,548,667 B2 | 2/2020 | Flett et al. |
| 10,555,777 B2 | 2/2020 | Griffiths et al. |
| 10,572,733 B2 | 2/2020 | Wells et al. |
| 10,575,910 B2 | 3/2020 | Itkowitz et al. |
| 10,595,880 B2 | 3/2020 | Otto et al. |
| 10,595,887 B2 | 3/2020 | Shelton et al. |
| 10,595,952 B2 | 3/2020 | Forrest et al. |
| 10,610,310 B2 | 4/2020 | Todd et al. |
| 10,610,315 B2 | 4/2020 | Itkowitz et al. |
| 10,610,316 B2 | 4/2020 | Swarup et al. |
| 10,617,479 B2 | 4/2020 | Itkowitz et al. |
| 10,624,807 B2 | 4/2020 | Itkowitz et al. |
| 10,638,970 B2 | 5/2020 | Obma et al. |
| 10,739,963 B2 | 8/2020 | Nikou et al. |
| 10,765,384 B2 | 9/2020 | Wollowick et al. |
| 2002/0055918 A1 | 5/2002 | Hlathein et al. |
| 2004/0260301 A1 | 12/2004 | Lionberger et al. |
| 2005/0020941 A1 | 1/2005 | Tarabichi |
| 2005/0113846 A1 | 5/2005 | Carson |
| 2005/0119661 A1 | 6/2005 | Hodgson et al. |
| 2005/0149040 A1 | 7/2005 | Haines et al. |
| 2005/0171545 A1 | 8/2005 | Walsh et al. |
| 2005/0234466 A1 | 10/2005 | Stallings |
| 2005/0251148 A1 | 11/2005 | Friedrich et al. |
| 2006/0015120 A1 | 1/2006 | Richard et al. |
| 2006/0064043 A1 | 3/2006 | Goeggelmann et al. |
| 2006/0200026 A1 | 9/2006 | Wallace et al. |
| 2006/0241405 A1 | 10/2006 | Leitner et al. |
| 2007/0073136 A1 | 3/2007 | Metzger |
| 2007/0123896 A1 | 5/2007 | Wyss et al. |
| 2007/0179626 A1 | 8/2007 | De La Barrera et al. |
| 2007/0244488 A1 | 10/2007 | Metzger et al. |
| 2008/0208081 A1 | 8/2008 | Murphy et al. |
| 2008/0249394 A1 | 10/2008 | Giori et al. |
| 2008/0281301 A1 | 11/2008 | Deboer et al. |
| 2008/0281328 A1 | 11/2008 | Lang et al. |
| 2008/0281426 A1 | 11/2008 | Fitz et al. |
| 2010/0063508 A1 | 3/2010 | Borja et al. |
| 2010/0064216 A1 | 3/2010 | Borja et al. |
| 2010/0145344 A1 | 6/2010 | Jordan et al. |
| 2011/0029091 A1 | 2/2011 | Bojarski et al. |
| 2011/0071528 A1 | 3/2011 | Carson |
| 2011/0071530 A1 | 3/2011 | Carson |
| 2011/0304332 A1 | 12/2011 | Mahfouz |
| 2011/0306986 A1 | 12/2011 | Lee et al. |
| 2012/0143084 A1 | 6/2012 | Shoham |
| 2012/0176306 A1 | 7/2012 | Lightcap et al. |
| 2012/0226198 A1 | 9/2012 | Carson |
| 2012/0226481 A1 | 9/2012 | Carson |
| 2013/0072821 A1 | 3/2013 | Odermatt et al. |
| 2013/0085510 A1 | 4/2013 | Stefanchik et al. |
| 2013/0144570 A1* | 6/2013 | Axelson, Jr. .......... A61B 90/36 703/1 |
| 2013/0209953 A1 | 8/2013 | Arlinsky et al. |
| 2014/0031664 A1 | 1/2014 | Kang et al. |
| 2014/0039520 A1 | 2/2014 | Haider et al. |
| 2014/0073907 A1 | 3/2014 | Kumar et al. |
| 2014/0108983 A1 | 4/2014 | William R et al. |
| 2014/0128727 A1 | 5/2014 | Daon et al. |
| 2014/0135791 A1 | 5/2014 | Nikou et al. |
| 2014/0188240 A1 | 7/2014 | Lang et al. |
| 2014/0189508 A1 | 7/2014 | Granchi et al. |
| 2014/0296871 A1 | 10/2014 | Chen et al. |
| 2015/0105782 A1 | 4/2015 | D'Lima et al. |
| 2015/0106024 A1 | 4/2015 | Lightcap et al. |
| 2016/0022374 A1 | 1/2016 | Haider et al. |
| 2016/0220175 A1 | 8/2016 | Tam et al. |
| 2016/0278754 A1 | 9/2016 | Todorov et al. |
| 2016/0278868 A1 | 9/2016 | Berend et al. |
| 2016/0338777 A1 | 11/2016 | Penenberg et al. |
| 2016/0354161 A1* | 12/2016 | Deitz .................... A61B 34/20 |
| 2017/0014169 A1 | 1/2017 | Dean et al. |
| 2017/0042557 A1 | 2/2017 | Plaskos et al. |
| 2017/0061375 A1 | 3/2017 | Laster et al. |
| 2017/0196571 A1 | 7/2017 | Berend et al. |
| 2017/0258532 A1 | 9/2017 | Shalayev et al. |
| 2017/0312099 A1 | 11/2017 | Paszicsnyek |
| 2017/0325973 A1 | 11/2017 | Bonny et al. |
| 2017/0340389 A1 | 11/2017 | Otto et al. |
| 2017/0347922 A1 | 12/2017 | Bhandari |
| 2017/0348008 A1 | 12/2017 | Lavallee et al. |
| 2018/0064496 A1 | 3/2018 | Hladio et al. |
| 2018/0071049 A1 | 3/2018 | Nowatschin et al. |
| 2018/0085135 A1 | 3/2018 | Singh et al. |
| 2018/0116805 A1 | 5/2018 | Johannaber et al. |
| 2018/0116823 A1 | 5/2018 | Johannaber et al. |
| 2018/0132940 A1* | 5/2018 | Kao .................... G06F 3/0482 |
| 2018/0132949 A1 | 5/2018 | Merette et al. |
| 2018/0168750 A1 | 6/2018 | Staunton et al. |
| 2018/0168762 A1 | 6/2018 | Scheib et al. |
| 2018/0177512 A1 | 6/2018 | Hogan et al. |

(56) References Cited

U.S. PATENT DOCUMENTS

| | | | |
|---|---|---|---|
| 2018/0199995 A1 | 7/2018 | Odermatt et al. | |
| 2018/0214180 A1 | 8/2018 | Theodore et al. | |
| 2018/0256256 A1 | 9/2018 | May et al. | |
| 2018/0317898 A1 | 11/2018 | Plaskos et al. | |
| 2018/0338796 A1 | 11/2018 | Yao et al. | |
| 2018/0344409 A1 | 12/2018 | Bonny et al. | |
| 2018/0368930 A1 | 12/2018 | Esterberg et al. | |
| 2019/0000631 A1 | 1/2019 | Blankevoort et al. | |
| 2019/0008599 A1 | 1/2019 | Lynch et al. | |
| 2019/0066832 A1 | 2/2019 | Kang et al. | |
| 2019/0069962 A1 | 3/2019 | Tabandeh et al. | |
| 2019/0069963 A1 | 3/2019 | Azizian et al. | |
| 2019/0083191 A1 | 3/2019 | Gilhooley et al. | |
| 2019/0090952 A1 | 3/2019 | Bonny et al. | |
| 2019/0090962 A1 | 3/2019 | Boettner | |
| 2019/0099228 A1 | 4/2019 | Keller et al. | |
| 2019/0117156 A1 | 4/2019 | Howard et al. | |
| 2019/0117407 A1 | 4/2019 | Yang | |
| 2019/0122330 A1 | 4/2019 | Saget et al. | |
| 2019/0133695 A1 | 5/2019 | Hladio et al. | |
| 2019/0147128 A1 | 5/2019 | O'Connor | |
| 2019/0175283 A1 | 6/2019 | Bonny et al. | |
| 2019/0200900 A1 | 7/2019 | Thelen et al. | |
| 2019/0201101 A1 | 7/2019 | Hafez | |
| 2019/0201214 A1 | 7/2019 | Miller et al. | |
| 2019/0209079 A1 | 7/2019 | Delport | |
| 2019/0216520 A1 | 7/2019 | Babak et al. | |
| 2019/0223962 A1 | 7/2019 | Roldan et al. | |
| 2019/0224016 A1 | 7/2019 | Walker et al. | |
| 2019/0240045 A1 | 8/2019 | Couture | |
| 2019/0240046 A1 | 8/2019 | Couture | |
| 2019/0254756 A1 | 8/2019 | Zhang et al. | |
| 2019/0272917 A1 | 9/2019 | Couture et al. | |
| 2019/0274662 A1 | 9/2019 | Rockman et al. | |
| 2019/0274762 A1 | 9/2019 | Kim et al. | |
| 2019/0290198 A1 | 9/2019 | Belson et al. | |
| 2019/0311542 A1 | 10/2019 | Douglas et al. | |
| 2019/0325386 A1 | 10/2019 | Laster et al. | |
| 2019/0336220 A1 | 11/2019 | Hladio et al. | |
| 2019/0365481 A1 | 12/2019 | Otto et al. | |
| 2019/0374130 A1 | 12/2019 | Bydlon et al. | |
| 2019/0380792 A1 | 12/2019 | Poltaretskyi et al. | |
| 2019/0388153 A1 | 12/2019 | Running et al. | |
| 2019/0388157 A1 | 12/2019 | Shameli et al. | |
| 2020/0000400 A1 | 1/2020 | Mckinnon et al. | |
| 2020/0015598 A1 | 1/2020 | Hondori et al. | |
| 2020/0060772 A1 | 2/2020 | Konh et al. | |
| 2020/0060773 A1 | 2/2020 | Barral et al. | |
| 2020/0100848 A1 | 4/2020 | Zuhars et al. | |
| 2020/0113583 A1 | 4/2020 | Philipp et al. | |
| 2020/0305978 A1 | 10/2020 | Tan et al. | |
| 2020/0352529 A1 | 11/2020 | Wollowick et al. | |
| 2021/0059656 A1 | 3/2021 | Otto et al. | |
| 2021/0192759 A1 * | 6/2021 | Lang | A61B 90/37 |
| 2021/0216822 A1 * | 7/2021 | Paik | G10L 15/22 |
| 2022/0172818 A1 | 6/2022 | Fanson et al. | |

FOREIGN PATENT DOCUMENTS

| | | | | |
|---|---|---|---|---|
| EP | 1 518 501 A2 | 3/2005 | | |
| EP | 1690503 A1 * | 8/2006 | | A61B 90/92 |
| EP | 1 226 788 B1 | 10/2006 | | |
| EP | 1 755 466 B1 | 12/2007 | | |
| EP | 2 007 291 A2 | 12/2008 | | |
| EP | 2 156 794 A1 | 2/2010 | | |
| EP | 2 384 714 A1 | 11/2011 | | |
| EP | 1 919 390 B1 | 12/2012 | | |
| EP | 1 841 372 B1 | 9/2017 | | |
| EP | 3 334 383 B1 | 4/2020 | | |
| WO | WO-9531148 A1 * | 11/1995 | | A61B 90/10 |
| WO | WO-2004/070580 A2 | 8/2004 | | |
| WO | WO-2006/078236 A1 | 7/2006 | | |
| WO | WO-2007/092841 A1 | 8/2007 | | |
| WO | WO-2012/082164 A1 | 6/2012 | | |
| WO | WO-2012082615 A2 * | 6/2012 | | H04N 7/183 |
| WO | WO-2012/101286 A1 | 8/2012 | | |
| WO | WO-2015/057814 A1 | 4/2015 | | |
| WO | WO-2016146768 A1 * | 9/2016 | | B25J 9/1676 |
| WO | WO-2016/198844 A1 | 12/2016 | | |
| WO | WO-2017/076886 A1 | 5/2017 | | |
| WO | WO-2017/108776 A1 | 6/2017 | | |
| WO | WO-2017/115235 A1 | 7/2017 | | |
| WO | WO-2017/124043 A1 | 7/2017 | | |
| WO | WO-2017/147596 A1 | 8/2017 | | |
| WO | WO-2017/179075 A1 | 10/2017 | | |
| WO | WO-2018/085694 A1 | 5/2018 | | |
| WO | WO-2018/085900 A1 | 5/2018 | | |
| WO | WO-2018/095499 A1 | 5/2018 | | |
| WO | WO-2018/104704 A1 | 6/2018 | | |
| WO | WO-2018/161120 A1 | 9/2018 | | |
| WO | WO-2019/006370 A1 | 1/2019 | | |
| WO | WO-2019/032828 A2 | 2/2019 | | |
| WO | WO-2019/068194 A1 | 4/2019 | | |
| WO | WO-2019/079634 A1 | 4/2019 | | |
| WO | WO-2019/081915 A1 | 5/2019 | | |
| WO | WO-2019/135805 A1 | 7/2019 | | |
| WO | WO-2019/148154 A1 | 8/2019 | | |
| WO | WO-2019/191722 A1 | 10/2019 | | |
| WO | WO-2019/224745 A1 | 11/2019 | | |
| WO | WO-2019/241516 A1 | 12/2019 | | |
| WO | WO-2019/245849 A1 | 12/2019 | | |
| WO | WO-2019/245851 A1 | 12/2019 | | |
| WO | WO-2020/033568 A2 | 2/2020 | | |
| WO | WO-2020/056443 A1 | 3/2020 | | |
| WO | WO-2020065209 A1 * | 4/2020 | | G05B 13/04 |
| WO | WO-2020/227832 A1 | 11/2020 | | |

OTHER PUBLICATIONS

Merriam-Webster, Definition of Robot, Dated: Nov. 12, 2020, Merriam-Webster.com Dictionary, Retrieved from archive.org at: https://web.archive.org/web/20201112024540/https://www.merriam-webster.com/dictionary/robot.*

Billinghurst et al. Tangible Augmented Reality, Year: 2008, International Conference on Computer Graphics and Interactive Techniques, 12 pages, Retrieved from: https://www.researchgate.net/publication/228344366_Tangible_augmented_reality.*

Alexander Tauchen, "Surgery to Replace a Bad Joint", Jul. 26, 2022, Illinois Bone & Joint Institute.*

Roche, Robotic and Sensor-Assisted Technologies in Knee Arthroplasty,, Holy Cross Hospital Orthopedic Institute, Operative Techniques in Orthopaedics, pp. 127-147 (Year: 2015).*

International Search Report and Written Opinion for International Application No. PCT/US2021/057353, mailed Feb. 11, 2022, 14 pages.

* cited by examiner

300

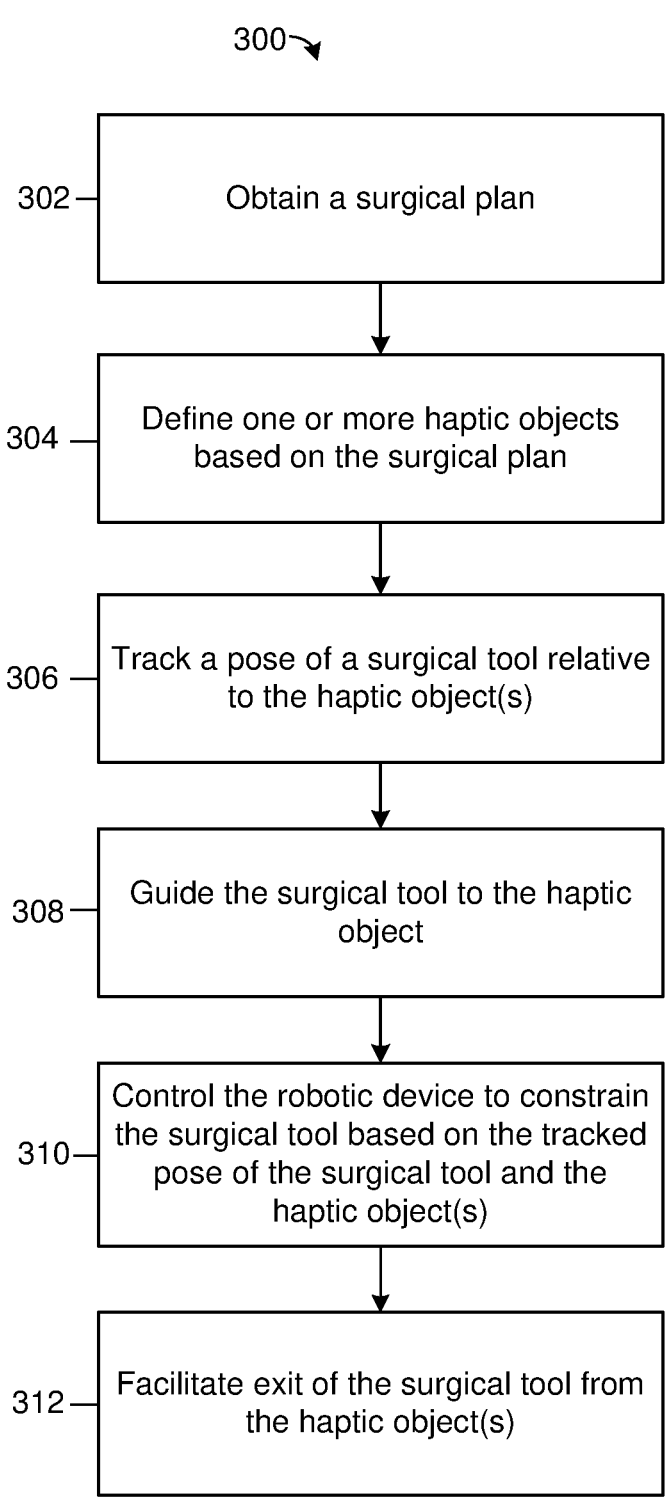

302 — Obtain a surgical plan

304 — Define one or more haptic objects based on the surgical plan

306 — Track a pose of a surgical tool relative to the haptic object(s)

308 — Guide the surgical tool to the haptic object

310 — Control the robotic device to constrain the surgical tool based on the tracked pose of the surgical tool and the haptic object(s)

312 — Facilitate exit of the surgical tool from the haptic object(s)

| Warning | Legend | Info Box Message |
|---------|--------|------------------|
| Notching | ◇ | ▪ Anterior cut notches bone<br>▪ Anterior cut <5° from bone |
| Airballing | ○ | Flange tip proud of bone >1mm |
| Size Mismatch | ⇄ | Combined implant size > 1 |
| Checkpoint | ⊗ | ▪ Femur checkpoint near cut<br>▪ Tibia checkpoint near cut |
| Combined Flexion | — | Combined flexion > 8° / 10° |
| Joint Line | ⊟ | Joint line outside range |
| Outside Planning Limits | | ▪ Femur plan outside range<br>▪ Tibia plan outside range |
| Captured Points | ● | Collected points > 100 |
| Gap Threshold | ▬ | Gap outside range |
| Overhang | ≫ | ▪ Femur plan overhangs >2mm<br>▪ Tibia plan overhangs >1mm |
| Floating | ▲ | ▪ Femur plan proud of existing cut<br>▪ Tibia plan proud of existing cut |
| Limb Alignment | | Planned alignment outside range |
| Laxity | | Planned laxity outside range |

FIG. 13

From step 408

1400

Receive surgeon selection — 1402

Receive a range of a surgical parameter preference — 1404

Compare the range of the surgical parameter preference to planned parameter value — 1406

Is the planned parameter value within the range? — 1408

YES → Remove any applicable warnings — 1410 → To step 410

NO

Generate a warning — 1412

Update implant plan or surgical parameter preference — 1414

From step 408

1600

Display preset anchor points for implant rotation — 1602

Receive a selection of a preset anchor point — 1604

Receive command to rotate the implant about the selected preset anchor point — 1606

Display image of implant based on the rotation — 1608

To step 410

SURGEON PREFERENCES AND WARNING VISUALIZATIONS FOR IMPLANT PLANNING

CROSS-REFERENCE TO RELATED APPLICATIONS

This application claims the benefit of and priority to U.S. Provisional Patent Application No. 63/125,468 filed Dec. 15, 2020, U.S. Provisional Patent Application No. 63/177, 034 filed Apr. 20, 2021, and U.S. Provisional Patent Application No. 63/226,858 filed Jul. 29, 2021, the entire disclosures of which are incorporated by reference herein.

BACKGROUND

The present disclosure relates generally to surgical systems for orthopedic surgeries, for example surgical systems that facilitate joint replacement procedures. Joint replacement procedures (arthroplasty procedures) are widely used to treat osteoarthritis and other damage to a patient's joint by replacing portions of the joint with prosthetic components. Joint replacement procedures can include procedures to replace hips, knees, shoulders, or other joints with one or more prosthetic components.

One possible tool for use in an arthroplasty procedure is a robotically-assisted surgical system. A robotically-assisted surgical system typically includes a robotic device that is used to prepare a patient's anatomy to receive an implant, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. Based on the surgical plan, the surgical system guides, controls, or limits movements of the surgical tool during portions of the surgical procedure. Guidance and/or control of the surgical tool serves to assist the surgeon during implementation of the surgical plan. Various features enabling improved planning, improved intra-operative assessments of the patient biomechanics, intraoperative plan adjustments, etc. for use with robotically-assisted surgical systems or other computer-assisted surgical systems may be advantageous.

BRIEF DESCRIPTION OF THE DRAWINGS

FIG. 3 is a flowchart of a first process that can be executed by the surgical system of FIG. 2, according to an exemplary embodiment.

FIG. 13 is an illustration of a table showing various icons that correspond to warnings, according to an exemplary embodiment.

SUMMARY

Figure 1:
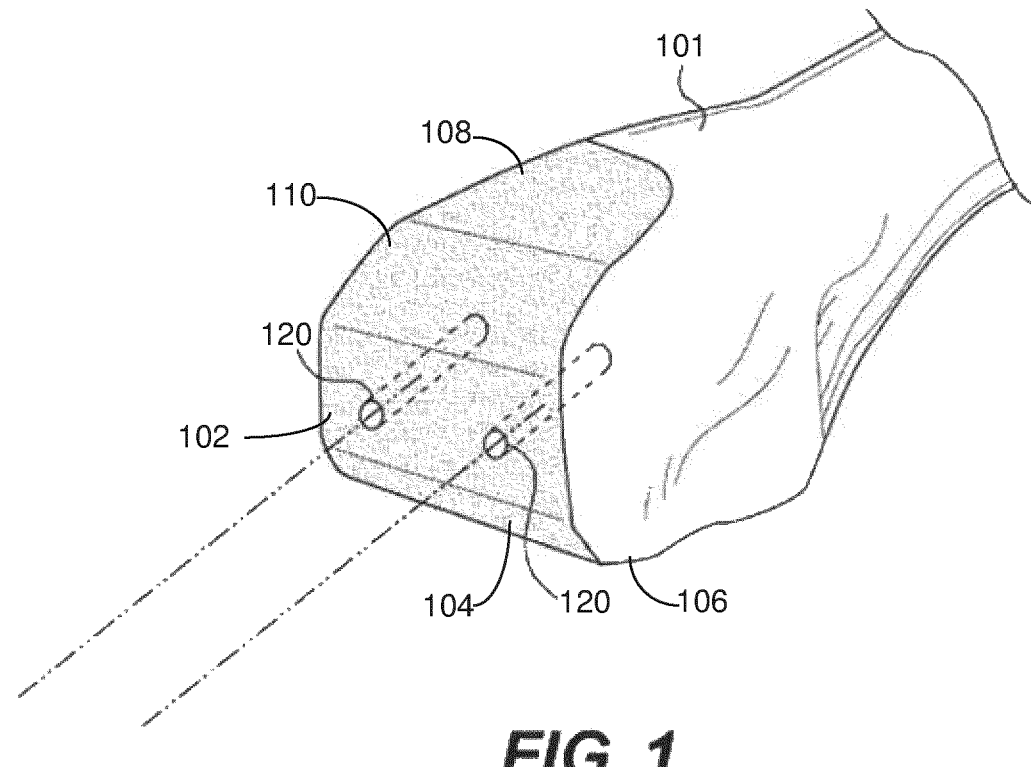
FIG. 1 is a perspective view of a femur prepared to receive an implant component, according to an exemplary embodiment.

A method for controlling a robotic system to facilitate a joint arthroplasty procedure includes generating a graphical user interface comprising a visualization of an implant plan and an indication of a user-defined value for an implant planning parameter, and comparing the user-defined value for the implant planning parameter to the range. In response to determining that the planned value is outside the range, the method includes providing a marking at the indication of the user-defined value on the graphical user interface, and receiving, from the graphical user interface, an update to the implant plan, wherein the update to the implant plan causes a change in the user-defined value. The method further includes determining that the change in the user-defined value moved the user-defined value to within the selected preferred range, and controlling a surgical system to facilitate the joint arthroplasty procedure based on the update to the implant plan.

In some implementations, the method further comprises removing the marking from the graphical user interface upon determining that the update to the implant plan moved the user-defined value to within the selected preferred range.

In some implementations, a first marking is associated with a first user-defined value that is outside the range and a second marking is associated with a second user-defined value that is outside the range, the first marking being different than the second marking.

In some implementations, the graphical user interface comprises a first text corresponding to the first marking and a second text corresponding to the second marking, the first text and the second text being located away from the first user-defined value and the second user-defined value.

In some implementations, selecting the first text via the graphical user interface causes the first marking to be emphasized on the graphical user interface and selecting the second text via the graphical user interface causes the second marking to be emphasized on the graphical user interface.

In some implementations, the visualization of the implant plan comprises a graphical representation of an implant positioned relative to a bone, and receiving the update to the implant plan comprises automatically identifying a first rotation point based on a first landmark positioned on the graphical representation of the implant. Receiving the update to the implant plan further comprises providing a first hotkey indicator at the first rotation point, the first hotkey indicator showing a first key to be pressed to select the first rotation point, and receiving a signal indicative of a press of the first key by the user. Receiving the updated to the implant plant further comprises allowing the user to rotate the graphical representation of the implant about the first rotation point.

In some implementations, a second rotation point is automatically identified based on a second landmark positioned on the graphical representation of the implant and a second hotkey indicator is provided at the second rotation point, the second hotkey indicator showing a second key to be pressed to select the second rotation point. The first hotkey indicator and the second hotkey indicator are different, and the first hotkey indicator is always in the same position relative to the second hotkey indicator.

A system for facilitating a joint arthroplasty procedure includes a robotic device configured to perform the joint arthroplasty procedure and a computer system in communication with the robotic device. The system includes a computer system having a processor and a memory device. The memory device contains instructions that, when executed by the processor, cause the processor to generate a graphical user interface including a visualization of an implant in a planned pose relative to a bone model, compare the planned pose to a plurality of criteria associated with a plurality of types of warnings to identify at least a first warning to provide via the graphical user interface, identify a particular symbol associated with the first warning from a plurality of symbols associated with the plurality of types of warnings, provide the particular symbol on the graphical user interface such that the particular symbol overlays the visualization of the implant at a position associated with violation of a first criteria of the plurality of criteria associated with the first warning, receive, from the graphical user interface, an update to the implant plan, wherein the update resolves the first warning, and control a surgical system to facilitate the joint arthroplasty procedure based on the update to the implant plan.

In some embodiments, the processor is further caused to remove the marking from the graphical user interface upon determining that the change in the implant plan resolved the first warning. In some embodiments, the plurality of types of warnings include a notching warning, an airball warning, and an overhang warning. In some embodiments, the plurality of types of warnings include a checkpoint warning, and the processor is further caused to compare the planned pose to a checkpoint criterion associated with the checkpoint warning by determining a distance between a cut plane associated with the planned pose and a position of a checkpoint on the bone model.

In some embodiments, upon selection of first text associated with the first warning via the graphical user interface, the processor is further caused to cause the first symbol to be emphasized on the graphical user interface. In some embodiments, the processor is further caused to automatically identify a first rotation point at a first landmark of the implant or the bone model, provide a first hotkey indicator at the first rotation point with the first hotkey indicator showing a first key to be pressed to select the first rotation point, receive a signal indicative of a press of the first key by the user, and allow the user to rotate the visualization of the implant about the first rotation point. In some embodiments, the processor is further caused to automatically identify a second rotation point based on a second landmark of the implant or the bone model, and provide a second hotkey indicator at the second rotation point with the second hotkey indicator showing a second key to be pressed to select the second rotation point. The first hotkey indicator and the second hotkey indicator are different, for example such that the first hotkey indicator is always in a same position relative to the second hotkey indicator.

A navigation system includes a controller programmed to select a range from a set of user-specific ranges by generating a graphical user interface comprising a visualization of an implant plan and an indication of a user-defined value for an implant planning parameter. The controller is further programmed to compare the user-defined value for the implant planning parameter to the range, and in response to determining that the user-defined value is outside the range, provide a marking at the indication of the user-defined value on the graphical user interface. The controller is further programmed to receive, from the graphical user interface, an update to the implant plan, wherein the update to the implant plan causes a change in the user-defined value, and determine that the change in the user-defined value moved the user-defined value to within the selected preferred range. The controller is further programmed to control a surgical system to facilitate the joint arthroplasty procedure based on the update to the implant plan.

In some implementations, the controller is further programmed to remove the marking from the graphical user interface upon determining that the update to the implant plan moved the user-defined value to within the selected preferred range.

In some implementations, a first marking is associated with a first user-defined value that is outside the range and a second marking is associated with a second user-defined value that is outside the range, the first marking being different than the second marking.

In some implementations, the graphical user interface comprises a first text corresponding to the first marking and a second text corresponding to the second marking, the first text and the second text being located away from the first user-defined value and the second user-defined value.

In some implementations, upon selecting the first text via the graphical user interface the controller is further programmed to cause the first marking to be emphasized on the graphical user interface and upon selecting the second text via the graphical user interface the controller is further programmed to cause the second marking to be emphasized on the graphical user interface.

In some implementations, the controller is further programmed to automatically identify a first rotation point based on a first landmark positioned on a graphical representation of an implant positioned relative to a bone and provide a first hotkey indicator at the first rotation point, the first hotkey indicator showing a first key to be pressed to select the first rotation point. The controller is further programmed to receive a signal indicative of a press of the first key by the user and allow the user to rotate the graphical representation of the implant about the first rotation point.

DETAILED DESCRIPTION

Presently preferred embodiments of the invention are illustrated in the drawings. An effort has been made to use the same or like reference numbers throughout the drawings to refer to the same or like parts. Although this specification refers primarily to a robotic arm for orthopedic joint replacement, it should be understood that the subject matter described herein is applicable to other types of robotic systems, including those used for non-surgical applications, as well as for procedures directed to other anatomical regions, for example spinal or dental procedures.

Referring now to FIG. 1, a femur 101 as modified during a knee arthroplasty procedure is shown, according to an exemplary embodiment. As shown in FIG. 1, the femur 101 has been modified with multiple planar cuts. In the example shown, the femur 100 has been modified by five substantially planar cuts to create five substantially planar surfaces, namely distal surface 102, posterior chamfer surface 104, posterior surface 106, anterior surface 108, and anterior chamfer surface 110. The planar surfaces may be achieved using a sagittal saw or other surgical tool, for example a surgical tool coupled to a robotic device as in the examples described below. The planar surfaces 102-110 are created such that the planar surfaces 102-110 will mate with corresponding surfaces of a femoral implant component. The positions and angular orientations of the planar surfaces 102-110 may determine the alignment and positioning of the implant component. Accordingly, operating a surgical tool to create the planar surfaces 102-110 with a high degree of accuracy may improve the outcome of a joint replacement procedure.

As shown in FIG. 1, the femur 101 has also been modified to have a pair of pilot holes 120. The pilot holes 120 extend into the femur 101 and are created such that the pilot holes 120 can receive a screw, a projection extending from a surface of an implant component, or other structure configured to facilitate coupling of an implant component to the femur 101. The pilot holes 120 may be created using a drill, spherical burr, or other surgical tool as described below. The pilot holes 120 may have a pre-planned position, orientation, and depth, which facilitates secure coupling of the implant component to the bone in a desired position and orientation. In some cases, the pilot holes 120 are planned to intersect with higher-density areas of a bone and/or to avoid other implant components and/or sensitive anatomical features. Accordingly, operating a surgical tool to create the pilot holes 120 with a high degree of accuracy may improve the outcome of a joint replacement procedure.

A tibia may also be modified during a joint replacement procedure. For example, a planar surface may be created on the tibia at the knee joint to prepare the tibia to mate with a tibial implant component. In some embodiments, one or more pilot holes or other recess (e.g., fin-shaped recess) may also be created in the tibia to facilitate secure coupling of an implant component tot eh bone.

In some embodiments, the systems and methods described herein provide robotic assistance for creating the planar surfaces 102-110 and the pilot holes 120 at the femur, and/or a planar surface and/or pilot holes 120 or other recess on a tibia. It should be understood that the creation of five planar cuts and two cylindrical pilot holes as shown in FIG.

1 is an example only, and that the systems and methods described herein may be adapted to plan and facilitate creation of any number of planar or non-planar cuts, any number of pilot holes, any combination thereof, etc., for preparation of any bone and/or joint in various embodiments. For example, in a hip or shoulder arthroplasty procedure, a spherical burr may be used in accordance with the systems and methods herein to ream a curved surface configured to receive a curved implant cup. Furthermore, in other embodiments, the systems and methods described herein may be used to facilitate placement an implant component relative to a bone (e.g., to facilitate impaction of cup implant in a hip arthroplasty procedure). Many such surgical and non-surgical implementations are within the scope of the present disclosure.

The positions and orientations of the planar surfaces 102-110, pilot holes 120, and any other surfaces or recesses created on bones of the knee joint can affect how well implant components mate to the bone as well as the resulting biomechanics for the patient after completion of the surgery. Tension on soft tissue can also be affected. Accordingly, systems and methods for planning the cuts which create these surfaces, facilitating intra-operative adjustments to the surgical plan, and providing robotic-assistance or other guidance for facilitating accurate creation of the planar surfaces 102-110, other surfaces, pilot holes 120, or other recesses can make surgical procedures easier and more efficient for healthcare providers and improve surgical outcomes.

Figure 2:
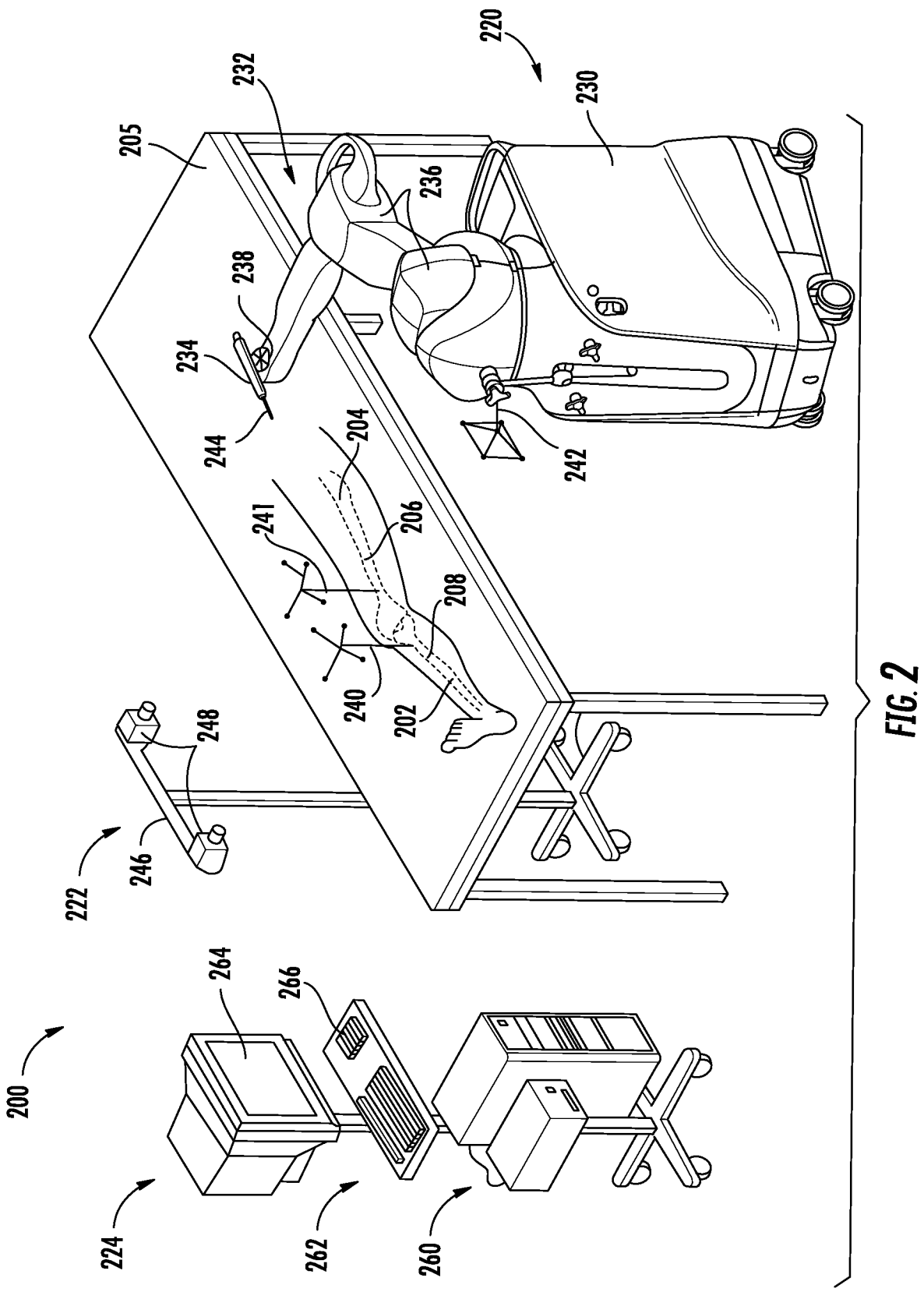
FIG. 2 is an illustration of a surgical system, according to an exemplary embodiment.

Referring now to FIG. 2, a surgical system 200 for orthopedic surgery is shown, according to an exemplary embodiment. In general, the surgical system 200 is configured to facilitate the planning and execution of a surgical plan, for example to facilitate a joint-related procedure. As shown in FIG. 2, the surgical system 200 is set up to treat a leg 202 of a patient 204 sitting or lying on table 205. In the illustration shown in FIG. 2, the leg 202 includes femur 206 (e.g., femur 101 of FIG. 1) and tibia 208, between which a prosthetic knee implant is to be implanted in a total knee arthroscopy procedure. In other scenarios, the surgical system 200 is set up to treat a hip of a patient, i.e., the femur and the pelvis of the patient. Additionally, in still other scenarios, the surgical system 200 is set up to treat a shoulder of a patient, i.e., to facilitate replacement and/or augmentation of components of a shoulder joint (e.g., to facilitate placement of a humeral component, a glenoid component, and a graft or implant augment). Various other anatomical regions and procedures are also possible.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 220 is an autonomous or semi-autonomous robot. "Autonomous"

refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 224, may autonomously complete the series of femoral cuts mentioned above without direct human intervention.

The robotic device 220 includes a base 230, a robotic arm 232, and a surgical tool 234, and is communicably coupled to the computing system 224 and the tracking system 222. The base 230 provides a moveable foundation for the robotic arm 232, allowing the robotic arm 232 and the surgical tool 234 to be repositioned as needed relative to the patient 204 and the table 205. The base 230 may also contain power systems, computing elements, motors, and other electronic or mechanical system necessary for the functions of the robotic arm 232 and the surgical tool 234 described below.

The robotic arm 232 is configured to support the surgical tool 234 and provide a force as instructed by the computing system 224. In some embodiments, the robotic arm 232 allows a user to manipulate the surgical tool and provides force feedback to the user. In such an embodiment, the robotic arm 232 includes joints 236 and mount 238 that include motors, actuators, or other mechanisms configured to allow a user to freely translate and rotate the robotic arm 232 and surgical tool 234 through allowable poses while providing force feedback to constrain or prevent some movements of the robotic arm 232 and surgical tool 234 as instructed by computing system 224. As described in detail below, the robotic arm 232 thereby allows a surgeon to have full control over the surgical tool 234 within a control object while providing force feedback along a boundary of that object (e.g., a vibration, a force preventing or resisting penetration of the boundary). In some embodiments, the robotic arm is configured to move the surgical tool to a new pose automatically without direct user manipulation, as instructed by computing system 224, in order to position the robotic arm as needed and/or complete certain surgical tasks, including, for example, cuts in a femur 206.

The surgical tool 234 is configured to cut, burr, grind, drill, partially resect, reshape, and/or otherwise modify a bone. The surgical tool 234 may be any suitable tool, and may be one of multiple tools interchangeably connectable to robotic device 220. For example, as shown in FIG. 2 the surgical tool 234 includes a spherical burr 244. In other examples, the surgical tool may also be a sagittal saw, for example with a blade aligned parallel with a tool axis or perpendicular to the tool axis. The surgical tool may also be a drill, for example with a rotary bit aligned parallel with a tool axis or perpendicular to the tool axis. The surgical tool 234 may also be a holding arm or other support configured to hold an implant component (e.g., cup 28a, implant augment, etc.) in position while the implant component is screwed to a bone, adhered (e.g., cemented) to a bone or other implant component, or otherwise installed in a preferred position. In some embodiments, the surgical tool 234 is an impaction tool configured to provide an impaction force to a cup implant to facilitate fixation of the cup implant to a pelvis in a planned location and orientation.

Tracking system 222 is configured track the patient's anatomy (e.g., femur 206 and tibia 208) and the robotic device 220 (i.e., surgical tool 234 and/or robotic arm 232) to enable control of the surgical tool 234 coupled to the robotic arm 232, to determine a position and orientation of modifications or other results made by the surgical tool 234, and allow a user to visualize the bones (e.g., femur 206, the tibia 208, pelvis, humerus, scapula, etc. as applicable in various procedures), the surgical tool 234, and/or the robotic arm 232 on a display of the computing system 224. The tracking system 222 can also be used to collect biomechanical measurements relating to the patient's anatomy, assess joint gap distances, identify a hip center point, assess native or corrected joint deformities, or otherwise collect information relating to the relative poses of anatomical features. More particularly, the tracking system 222 determines a position and orientation (i.e., pose) of objects (e.g., surgical tool 234, femur 206) with respect to a coordinate frame of reference and tracks (i.e., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials coupled to surgical tool 234, and a detection device 246 configured to detect the three-dimensional position of fiducials (i.e., markers on fiducial trees 240-242). Fiducial trees 240, 241 may be coupled to other bones as suitable for various procedures (e.g., pelvis and femur in a hip arthroplasty procedure). Detection device 246 may be an optical detector such as a camera or infrared sensor. The fiducial trees 240-242 include fiducials, which are markers configured to show up clearly to the optical detector and/or be easily detectable by an image processing system using data from the optical detector, for example by being highly reflective of infrared radiation (e.g., emitted by an element of tracking system 222). A stereoscopic arrangement of cameras on detection device 246 allows the position of each fiducial to be determined in 3D-space through a triangulation approach. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (i.e., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical tool 234 relative to a patient's anatomical feature, for example femur 206, as the surgical tool 234 is used to modify the anatomical feature or otherwise facilitate the surgical procedure. Additionally, using the tracking system 222 of FIG. 2 or some other approach to surgical navigation and tracking, the surgical system 200 can determine the relative poses of the tracked bones.

The computing system 224 is configured to create a surgical plan, control the robotic device 220 in accordance with the surgical plan to make one or more bone modifications and/or facilitate implantation of one or more prosthetic components. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer code for executing (e.g., by the processing circuit 260 and/or processor) one or more processes described herein.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed. The imaging data may be created using any suitable medical imaging technique to image the relevant anatomical feature, including computed tomography (CT), magnetic resonance imaging (MM), and/or ultrasound. The imaging data is then segmented (i.e., the regions in the imaging corresponding to different anatomical features are distinguished) to obtain the virtual bone model. For example, MM-based scan data of a joint can be segmented to distinguish bone from surrounding ligaments, cartilage, previously-implanted prosthetic components, and other tissue to obtain a three-dimensional model of the imaged bone.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.). In some embodiments, the surgical plan may be generated and/or modified based on distraction force measurements collected intraoperatively.

The preoperative surgical plan includes the desired cuts, holes, surfaces, burrs, or other modifications to a patient's anatomy to be made using the surgical system 200. For example, for a total knee arthroscopy procedure, the preoperative plan may include the cuts necessary to form, on a femur, a distal surface, a posterior chamfer surface, a posterior surface, an anterior surface, and an anterior chamfer surface in relative orientations and positions suitable to be mated to corresponding surfaces of the prosthetic to be joined to the femur during the surgical procedure, as well as cuts necessary to form, on the tibia, surface(s) suitable to mate to the prosthetic to be joined to the tibia during the surgical procedure. As another example, the preoperative plan may include the modifications necessary to create holes (e.g., pilot holes 120) in a bone. As another example, in a hip arthroplasty procedure, the surgical plan may include the burr necessary to form one or more surfaces on the acetabular region of the pelvis to receive a cup and, in suitable cases, an implant augment. Accordingly, the processing circuit 260 may receive, access, and/or store a model of the prosthetic to facilitate the generation of surgical plans. In some embodiments, the processing circuit facilitate intraoperative modifications tot eh preoperative plant.

The processing circuit 260 is further configured to generate a control object for the robotic device 220 in accordance with the surgical plan. The control object may take various forms according to the various types of possible robotic devices (e.g., haptic, autonomous). For example, in some embodiments, the control object defines instructions for the robotic device to control the robotic device to move within the control object (i.e., to autonomously make one or more cuts of the surgical plan guided by feedback from the tracking system 222). In some embodiments, the control object includes a visualization of the surgical plan and the robotic device on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical tool 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone. A curved haptic object may represent a resulting surface of a bone as modified to receive a cup implant and/or implant augment. A line haptic object may correspond to a pilot hole to be made in a bone to prepare the bone to receive a screw or other projection.

In an embodiment where the robotic device 220 is a haptic device, the processing circuit 260 is further configured to generate a virtual tool representation of the surgical tool 234. The virtual tool includes one or more haptic interaction points (HIPs), which represent and are associated with locations on the physical surgical tool 234. In an embodiment in which the surgical tool 234 is a spherical burr (e.g., as shown in FIG. 2), a HIP may represent the center of the spherical burr. Where one HIP is used to virtually represent a surgical tool, the HIP may be referred to herein as a tool center point (TCP). If the surgical tool 234 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to an "HIP" are deemed to also include references to "one or more HIPs." As described below, relationships between HIPs and haptic objects enable the surgical system 200 to constrain the surgical tool 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010, 180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 234 to a virtual tool representation of the surgical tool 234, so that the surgical system 200 can determine and monitor the pose of the surgical tool 234 relative to the patient (i.e., to femur 206). Registration of allows for accurate navigation, control, and/or force feedback during the surgical procedure.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical tool 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 to minimize the need to track and process motion of the femur 206.

For embodiments where the robotic device 220 is a haptic device, the surgical system 200 is configured to constrain the surgical tool 234 based on relationships between HIPs and haptic objects. That is, when the processing circuit 260 uses data supplied by tracking system 222 to detect that a user is manipulating the surgical tool 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical tool 234. In general, the term "constrain," as used herein, is used to describe a tendency to restrict movement. However, the form of constraint imposed on surgical tool 234 depends on the form of the relevant haptic object. A haptic object may be formed in any desirable shape or configuration. As noted above, three exemplary embodiments include a line, plane, or three-dimensional volume. In one embodiment, the surgical tool 234 is constrained because a HIP of surgical tool 234 is restricted to movement along a linear haptic object. In another embodiment, the haptic object is a three-dimensional volume and the surgical tool 234 may be constrained by substantially preventing movement of the HIP outside of the volume enclosed by the walls of the three-dimensional haptic object. In another embodiment, the surgical tool 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface on the femur 206 in order to confine the surgical tool 234 substantially to the plane needed to carry out the planned distal cut.

For embodiments where the robotic device 220 is an autonomous device, the surgical system 200 is configured to autonomously move and operate the surgical tool 234 in accordance with the control object. For example, the control object may define areas relative to the femur 206 for which a cut should be made. In such a case, one or more motors, actuators, and/or other mechanisms of the robotic arm 232 and the surgical tool 234 are controllable to cause the surgical tool 234 to move and operate as necessary within the control object to make a planned cut, for example using tracking data from the tracking system 222 to allow for closed-loop control.

Referring now to FIG. 3, a flowchart of a process 300 that can be executed by the surgical system 200 of FIG. 2 is shown, according to an exemplary embodiment. Process 300 may be adapted to facilitate various surgical procedures, including total and partial joint replacement surgeries.

At step 302, a surgical plan is obtained. The surgical plan (e.g., a computer-readable data file) may define a desired outcome of bone modifications, for example defined based on a desired position of prosthetic components relative to the patient's anatomy. For example, in the case of a knee arthroplasty procedure, the surgical plan may provide planned positions and orientations of the planar surfaces 102-110 and the pilot holes 120 as shown in FIG. 1. The surgical plan may be generated based on medical imaging, 3D modeling, surgeon input, etc.

At step 304, one or more control boundaries, such as haptic objects, are defined based on the surgical plan. The one or more haptic objects may be one-dimensional (e.g., a line haptic), two dimensional (i.e., planar), or three dimensional (e.g., cylindrical, funnel-shaped, curved, etc.). The haptic objects may represent planned bone modifications (e.g., a haptic object for each of the planar surfaces 102-110 and each of the pilot holes 120 shown in FIG. 1), implant components, surgical approach trajectories, etc. defined by the surgical plan. The haptic objects can be oriented and positioned in three-dimensional space relative to a tracked position of a patient's anatomy.

At step 306, a pose of a surgical tool is tracked relative to the haptic object(s), for example by the tracking system 222 described above. In some embodiments, one point on the surgical tool is tracked. In other embodiments, (e.g., in the example of FIGS. 4-5) two points on the surgical tool are tracked, for example a tool center point (TCP) at a tip/ effective end of the surgical tool and a second interaction point (SIP) positioned along a body or handle portion of the surgical tool. In other embodiments, three or more points on the surgical tool are tracked. A pose of the surgical tool is ascertained relative to a coordinate system in which the one or more haptic objects are defined and, in some embodiments, in which the pose of one or more anatomical features of the patient is also tracked.

At step 308, the surgical tool is guided to the haptic object(s). For example, the display 264 of the surgical system 200 may display a graphical user interface instructing a user on how (e.g., which direction) to move the surgical tool and/or robotic device to bring the surgical tool to a haptic object. As another example, the surgical tool may be guided to a haptic object using a collapsing haptic boundary as described in U.S. Pat. No. 9,289,264, the entire disclosure of which is incorporated by reference herein. As another example, the robotic device may be controlled to automatically move the surgical tool to a haptic object.

At step 310, the robotic device is controlled to constrain movement of the surgical tool based on the tracked pose of the surgical tool and the poses of one or more haptic objects. The constraining of the surgical tool may be achieved as described above with reference to FIG. 2.

At step 312, exit of the surgical tool from the haptic object(s) is facilitated, i.e., to release the constraints of a haptic object. For example, in some embodiments, the robotic device is controlled to allow the surgical tool to exit a haptic object along an axis of the haptic object. In some embodiments, the surgical tool may be allowed to exit the haptic object in a pre-determined direction relative to the haptic object. The surgical tool may thereby be removed from the surgical field and the haptic object to facilitate subsequent steps of the surgical procedure. Additionally, it should be understood that, in some cases, the process 300 may return to step 308 where the surgical tool is guided to the same or different haptic object after exiting a haptic object at step 312.

Process 300 may thereby be executed by the surgical system 200 to facilitate a surgical procedure. Features of process 300 are shown in FIGS. 4-18 below according to some embodiments, and such features can be combined in various combinations in various embodiments and/or based on settings selected for a particular procedure. Furthermore, it should be understood that the features of FIGS. 4-13 may be provided while omitting some or all other steps of process 300. All such possibilities are within the scope of the present disclosure.

Figure 4:
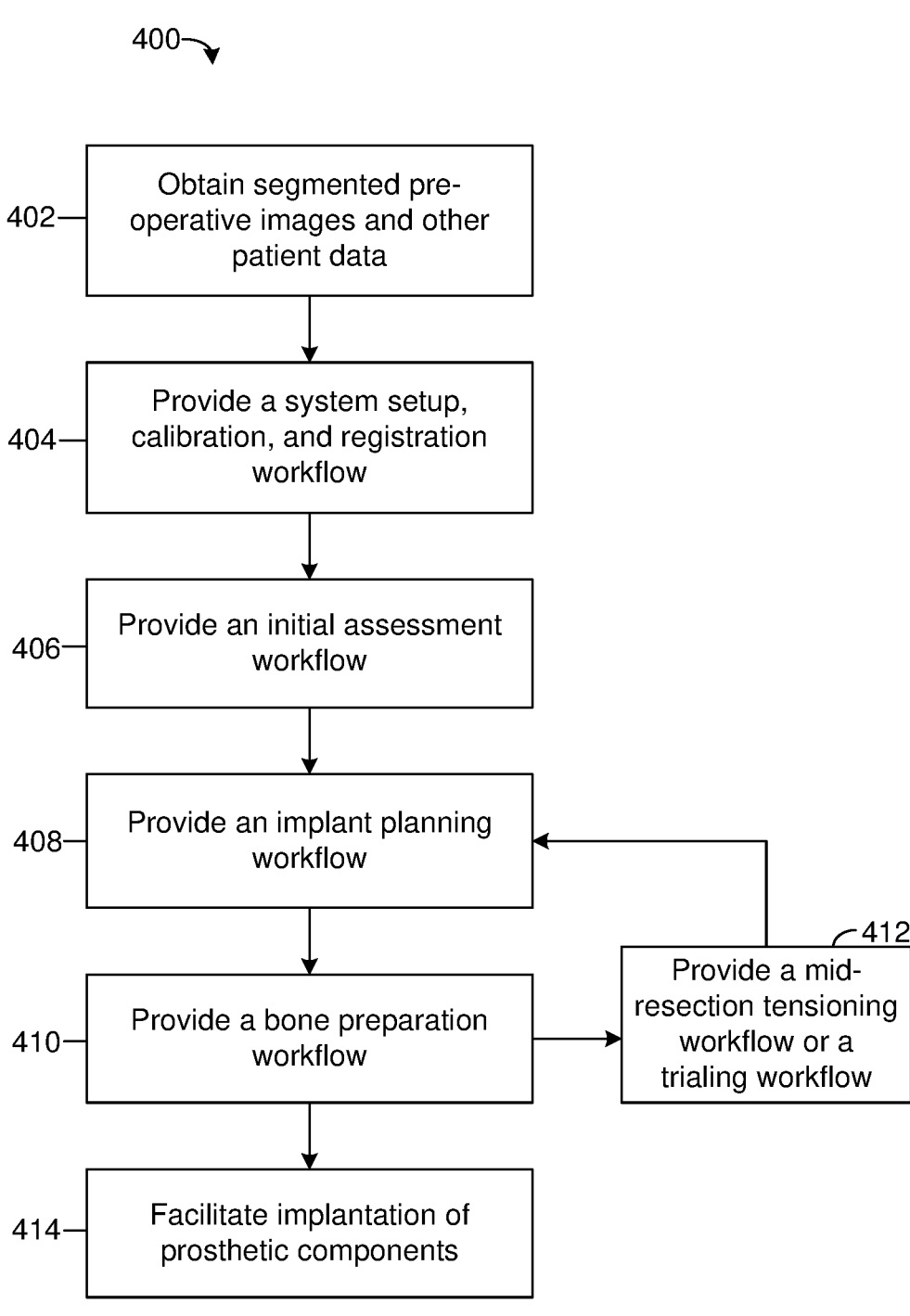
FIG. 4 is a flowchart of a second process that can be executed by the surgical system of FIG. 2, according to an exemplary embodiment.

Referring now to FIG. 4, a flowchart of a process 400 for facilitating surgical planning and guidance is shown, according to an exemplary embodiment. The process 400 may be executed by the surgical system 200 of FIG. 2, in some embodiments. In some cases, the process 300 is executed as part of executing the process 400.

At step 402, segmented pre-operative images and other patient data are obtained, for example by the surgical system 200. For example, segmented pre-operative CT images or MRI images may be received at the computing system 224 from an external server. In some cases, pre-operative images of a patient's anatomy are collected using an imaging device and segmented by a separate computing system and/or with manual user input to facilitate segmentation. In other embodiments, unsegmented pre-operative images are received at the computing system 224 and the computing system 224 is configured to automatically segment the images. The segmented pre-operative images can show the geometry, shape, size, density, and/or other characteristics of bones of a joint which is to be operated on in a procedure performed using process 400.

Other patient data can also be obtained at step 402. For example, the computing system 224 may receive patient information from an electronic medical records system. As another example, the computing system 224 may accept user input of patient information. The other patient data may include a patient's name, identification number, biographical information (e.g., age, weight, etc.), other health conditions, etc. In some embodiments, the patient data obtained at step 402 includes information specific to the procedure to be performed and the relevant pre-operative diagnosis. For example, the patient data may indicate which joint the procedure will be performed on (e.g., right knee, left knee). The patient data may indicate a diagnosed deformity, for example indicating whether a knee joint was diagnosed as having a varus deformity or a valgus deformity. This or other data that may facilitate the surgical procedure may be obtained at step 402.

At step 404, a system setup, calibration, and registration workflow is provided, for example by the surgical system 200. The system setup, calibration, and registration workflows may be configured to prepare the surgical system 220 for use in facilitating a surgical procedure. For example, at step 4040, the computer system 224 may operate to provide graphical user interfaces that include instructions for performing system setup, calibration, and registrations steps. The computer system 224 may also cause the tracking system 222 to collect tracking data and control the robotic device 220 to facilitate system setup, calibration, and/or registration. The computer system 224 may also receiving tracking data from the tracking system 222 and information from the computer system 224 and use the received information and data to calibrate the robotic device 220 and define various geometric relationships between tracked points (e.g., fiducials, markers), other components of the surgical system 200 (e.g., robotic arm 232, surgical tool 234, probe), and virtual representations of anatomical features (e.g., virtual bone models).

The system setup workflow provided at step 404 may include guiding the robotic device 220 to a position relative to a surgical table and the patient which will be suitable for completing an entire surgical procedure without repositioning the robotic device 220. For example, the computer system 224 may generate and provide a graphical user interface configured to provide instructions for moving a portable cart of the robotic device 220 into a preferred position. In some embodiments, the robotic device 220 can be tracked to determine whether the robotic device 220 is properly positioned. Once the cart is positioned, in some embodiments the robotic device 220 is controlled to automatically position the robotic arm 232 in a pose suitable for initiation of calibration and/or registration workflows.

The calibration and registration workflows provided at step 404 may include generating instructions for a user to perform various calibration and registration tasks while operating the tracking system 222 to generate tracking data. The tracking data can then be used to calibrate the tracking system 222 and the robotic device 220 and to register the first fiducial tree 240, second fiducial tree 241, and third fiducial tree 242 relative to the patient's anatomical features, for example by defining geometric relationships between the fiducial trees 240-242 and relevant bones of the patient in the example of FIG. 2. The registration workflow may include tracking a probe used to touch various points on the bones of a joint. In some embodiments, providing the registration workflow may include providing instructions to couple a checkpoint (e.g., a screw or pin configured to be contacted by a probe) to a bone and tracking a probe as the probe contacts the checkpoint and as the probe is used to paint (i.e., move along, touch many points along) one or more surfaces of the bone. The probe can be moved and tracked in order to collect points in or proximate the joint to be operated upon as well as at other points on the bone (e.g., at ankle or hip for a knee surgery).

In some embodiments, providing the registration workflow includes generating instructions to move the patient's leg to facilitate collection of relevant tracking data that can be used to identify the location of a biomechanical feature, for example a hip center point. Providing the registration workflow can include providing audio or visual feedback indicating whether the leg was moved in the proper manner to collect sufficient tracking data. Various methods and approaches for registration and calibration can be used in various embodiments. Step 404 may include steps performed before or after an initial surgical incision is made in the patient's skin to initiate the surgical procedure.

At step 406, an initial assessment workflow is provided, for example by the surgical system 200. The initial assessment workflow provides an initial assessment of the joint to be operated upon based on tracked poses of the bones of the joint. For example, the initial assessment workflow may include tracking relative positions of a tibia and a femur using data from the tracking system while providing real-time visualizations of the tibia and femur via a graphical user interface. The computing system 224 may provide instructions via the graphical user interface to move the tibia and femur to different relative positions (e.g., different degrees of flexion) and to exert different forces on the joint (e.g., a varus or valgus force). In some embodiments, the initial assessment workflow includes determine, by the surgical system 220 and based on data from the tracking system 222, whether the patient's joint has a varus or valgus deformity, and, in some embodiments, determining a magnitude of the deformity. In some embodiments, the initial assessment workflow may include collecting data relating to native ligament tension or native gaps between bones of the joint. In some embodiments, the initial assessment workflow may include displaying instructions to exert a force on the patient's leg to place the joint in a corrected state corresponding to a desired outcome for a joint arthroplasty procedure, and recording the relative poses of the bones and other relevant measurements while the joint is in the corrected state. The initial assessment workflow thereby results in collection of data that may be useful for the surgical system 200 or a surgeon in later steps of process 400.

At step 408, an implant planning workflow is provided, for example by the surgical system 200. The implant planning workflow is configured to facilitate users in planning implant placement relative to the patient's bones and/or planning bone cuts or other modifications for preparing bones to receive implant components. Step 408 may include generating, for example by the computing system 324, three-dimensional computer models of the bones of the joint (e.g., a tibia model and a femur model) based on the segmented medical images received at step 402. Step 408 may also include obtaining three-dimensional computer models of prosthetic components to be implanted at the joint (e.g., a tibial implant model and a femoral implant model). A graphical user interface can be generated showing multiple views of the three-dimensional bone models with the three-dimensional implant models shown in planned positions relative to the three-dimensional bone models. Providing the implant planning workflow can include enabling the user to adjust the position and orientation of the implant models relative to the bone models. Planned cuts for preparing the bones to allow the implants to be implanted at the planned positions can then be automatically based on the positioning of the implant models relative to the bone models.

The graphical user interface can include data and measurements from pre-operative patient data (e.g., from step 402) and from the initial assessment workflow (step 406) and/or related measurements that would result from the planned implant placement. The planned measurements (e.g., planned gaps, planned varus/valgus angles, etc.) can be calculated based in part on data collected via the tracking system 222 in other phases of process 400, for example from initial assessment in step 406 or trialing or tensioning workflows described below with reference to step 412.

The implant planning workflow may also include providing warnings (alerts, notifications) to users when an implant plan violates various criteria. In some cases, the criteria can be predefined, for example related to regulatory or system requirements that are constant for all surgeons and/or for all patients. In other embodiments, the criteria may be related to surgeon preferences, such that the criteria for triggering a warning can be different for different surgeons. In some cases, the computing system 224 can prevent the process 400 from moving out of the implant planning workflow when one or more of certain criteria are not met.

The implant planning workflow provided at step 408 thereby results in planned cuts for preparing a joint to receive prosthetic implant components. In some embodiments, the planned cuts include a planar tibial cut and multiple planar femoral cuts, for example as described above with reference to FIG. 1. The planned cuts can be defined relative to the virtual bone models used in the implant planning workflow at step 408. Based on registration processes from step 404 which define a relationship between tracked fiducial markers and the virtual bone models, the positions and orientations of the planned cuts can also be defined relative to the tracked fiducial markers, (e.g., in a coordinate system used by the tracking system 222). The surgical system 200 is thereby configured to associate the planned cuts output from step 408 with corresponding planes or other geometries in real space.

At step 410, a bone preparation workflow is provided, for example by the surgical system 200. The bone preparation workflow includes guiding execution of one or more cuts or other bone modifications based on the surgical plan created at step 408. For example, as explained in detail above with reference to FIGS. 2-3, the bone preparation workflow may include providing haptic feedback which constrains the surgical tool 234 to a plane associated with a planned cut to facilitate use of the surgical tool 234 to make that planned cut. In other embodiments, the bone preparation workflow can include automatically controlling the robotic device 220 to autonomously make one or more cuts or other bone modifications to carry out the surgical plan created at step 408. In other embodiments, the bone preparation workflow comprises causing the robotic device 200 to hold a cutting guide, drill guide, jig, etc. in a substantially fixed position that allows a separate surgical tool to be used to execute the planned cut while being confined by the cutting guide, drill guide, jig, etc. The bone preparation workflow can thus include control of a robotic device in accordance with the surgical plan.

The bone preparation workflow at step 410 can also include displaying graphical user interface elements configured to guide a surgeon in completing one or more planned cuts. For example, the bone preparation workflow can include tracking the position of a surgical tool relative to a plane or other geometry associated with a planned cut and relative to the bone to be cut. In this example, the bone preparation workflow can include displaying, in real-time, the relative positions of the surgical tool, cut plane or other geometry, and bone model. In some embodiments, visual, audio, or haptic warnings can be provided to indicate interruptions to performance of the planned cut, deviation from the planned cut, or violation of other criteria relating to the bone preparation workflow.

In some embodiments, step 410 is provided until all bone cuts planned at step 408 are complete and the bones are ready to be coupled to the implant components. In other embodiments, for example as shown in FIG. 4, a first iteration of step 410 can include performing only a portion of the planned cuts. For example, in a total knee arthroplasty procedure, a first iteration of step 410 can include making a tibial cut to provide a planar surface on the tibia without modifying the femur in the first iteration of step 410.

Following an iteration of the bone preparation workflow at step 410, the process 400 can proceed to step 412. At step 412 a mid-resection tensioning workflow or a trialing workflow is provided, for example by the surgical system 200. The mid-resection tensioning workflow is provided when less than all of the bone resection has been completed. The trialing workflow is provided when all resections have been made and/or bones are otherwise prepared to be temporarily coupled to trial implants. The mid-resection tensioning workflow and the trialing workflow at step 412 provide for collection of intraoperative data relating to relative positions of bones of the joint using the tracking system 222 including performing gap measurements or other tensioning procedures that can facilitate soft tissue balancing and/or adjustments to the surgical plan.

For example, step 412 may include displaying instructions to a user to move the joint through a range of motion, for example from flexion to extension, while the tracking system 222 tracks the bones. In some embodiments, gap distances between bones are determined from data collected by the tracking system 222 as a surgeon places the joint in both flexion and extension. In some embodiments, soft tissue tension or distraction forces are measured. Because one or more bone resections have been made before step 412 and soft tissue has been affected by the procedure, the mechanics of the joint may be different than during the initial assessment workflow of step 402 and relative to when the pre-operative imaging was performed. Accordingly, providing for intra-operative measurements in step 412 can provide information to a surgeon and to the surgical system 200 that was not available pre-operatively and which can be used to help fine tune the surgical plan.

From step 412, the process 400 returns to step 408 to provide the implant planning workflow again, now augmented with data collected during a mid-resection or trialing workflow at step 412. For example, planned gaps between implants can be calculated based on the intraoperative measurements collected at step 414, the planned position of a tibial implant relative to a tibia, and the planned position of a femoral implant relative to a femur. The planned gap values can then be displayed in an implant planning interface during step 408 to allow a surgeon to adjust the planned implant positions based on the calculated gap values. In various embodiments, a second iteration of step 408 to provide the implant planning workflow incorporates various data from step 412 in order to facilitate a surgeon in modifying and fine-tuning the surgical plan intraoperatively.

Steps 408, 410, and 412 can be performed multiple times to provide for intra-operative updates to the surgical plan based on intraoperative measurements collected between bone resections. For example, in some cases, a first iteration of steps 408, 410, and 412 includes planning a tibial cut in step 408, executing the planned tibial cut in step 410, and providing a mid-resection tensioning workflow in step 414. In this example, a second iteration of steps 408, 410, and 412 can include planning femoral cuts using data collected in the mid-resection tensioning workflow in step 408, executing the femoral cuts in step 410, and providing a trialing workflow in step 412. Providing the trialing workflow can include displaying instructions relating to placing trial implants on the prepared bone surfaces, and, in some embodiments, verifying that the trial implants are positioned in planned positions using the tracking system 222. Tracking data can be collected in a trialing workflow in step 412 relating to whether the trial implants are placed in acceptable positions or whether further adjustments to the surgical plan are needed by cycling back to step 408 and making further bone modifications in another iteration of step 410.

In some embodiments, executing process 400 can include providing users with options to jump between steps of the process 400 to enter a desired workflow. For example, a user can be allowed to switch between implant planning and bone preparation on demand. In other embodiments, executing process 400 can include ensuring that a particular sequence of steps of process 400 are followed. In various embodiments, any number of iterations of the various steps can be performed until a surgeon is satisfied that the bones have been properly prepared to receive implant components in clinically-appropriate positions.

As shown in FIG. 4, the process 400 includes step 414 where implantation of prosthetic components is facilitated. Once the bones have been prepared via step 410, the prosthetic components can be implanted. In some embodiments, step 414 is executed by the surgical system 200 by removing the robotic arm 232 from the surgical field and otherwise getting out of the way to allow a surgeon to fix the prosthetic components onto the bones without further assistance from the surgical system 200. In some embodiments, step 414 includes displaying instructions and/or navigational information that supports a surgeon in placing prosthetic components in the planned positions. In yet other embodiments, step 414 includes controlling the robotic arm 232 to place one or more prosthetic components in planned positions (e.g., holding a prosthetic component in the planned position while cement cures, while screws are inserted, constraining an impaction device to planned trajectory). Process 400 can thereby result in prosthetic components being affixed to modified bones according to an intra-operatively updated surgical plan.

Referring generally to the FIGURES, embodiments described herein provide systems and methods for a user (e.g., a surgeon or other medical professional) to indicate specific preferences related to a surgical procedure during or prior to the surgical planning workflow. In some embodiments the user can specify, via graphical user interface displayed on the display 264, preference ranges for varus or valgus angles between the tibia 208 and the femur 206, preference ranges for medial and lateral gaps between bones in flexion (e.g., when the femur 206 and the tibia 208 are bent towards each other) and extension (e.g., when the femur 206 and the tibia 208 are straightened), preference ranges for rotational amounts, preference ranges for resection amounts, preference ranges for joint line distances, and various other parameters associated with a particular surgery. The parameters listed above are related to a surgical procedure on the knee, but one of skill in the art would understand that the types of parameters that can be selected depends on the particular surgical procedure being performed or planned.

Furthermore, embodiments described herein provide systems and methods to warn the user when an actual or planned value is outside the preferred range(s) as defined by the user. The warnings can be provided on the graphical user interface via the display 246 as text, graphics, or a combination thereof. In embodiments where text is used as a warning, the text may be located in a particular portion of the graphical user interface (e.g., a warning box). In other embodiments where text is used as a warning, the text may be located adjacent to an image corresponding to the warning. In embodiments where a graphic is used as a warning, the graphic may be located on a virtual model of a surgical site (e.g., the femur 206 and/or the tibia 208) and may include text to clarify the warning. In some embodiments, the user may be able to select the warning in order to make modifications to one or more of the surgical plan or the preference ranges such that the warning is removed.

In addition, embodiments described herein provide systems and methods to manipulate a virtual model of a surgical procedure (e.g., a knee replacement procedure). The virtual model may be manipulated via a graphical user interface displayed on the display 246, and the virtual model may include preset anchor points that can be selected by the user to manipulate the virtual model around the preset anchor points.

Figure 5:
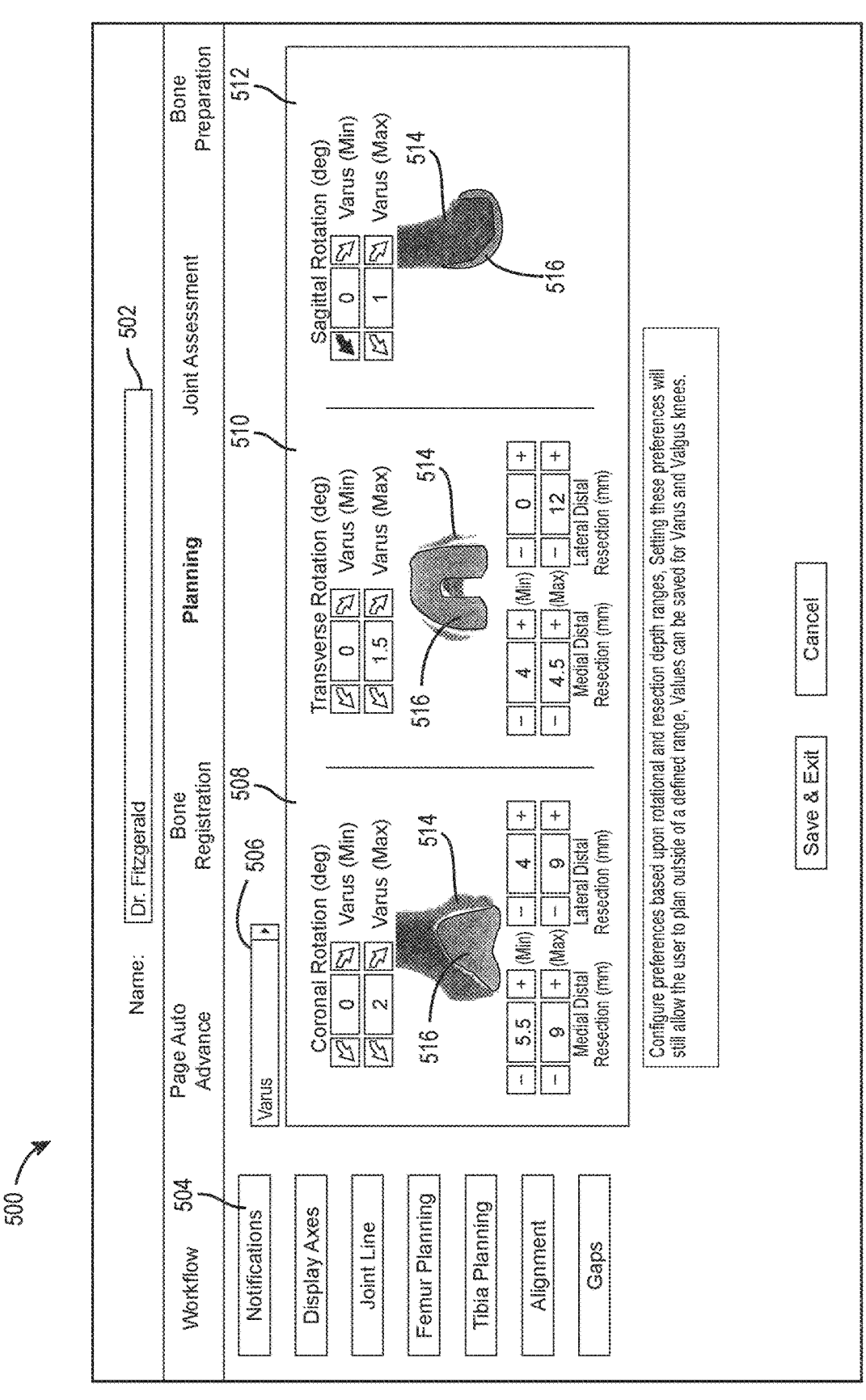
FIG. 5 is an illustration of a surgeon preference selection interface, according to an exemplary embodiment.

Referring now to FIG. 5, an illustration of a surgeon preference selection interface 500 is shown, according to an exemplary embodiment. In some embodiments, the surgeon preference selection interface 500 (e.g., "the interface 500") is displayed to a user via the display 246, and the user (e.g., a surgeon or other medical professional) can interact with the display 246 via the input/output device 262, which can include the keyboard 266 and a mouse (not shown). The interface 500 is shown to include a user selection portion 502, a selection menu 504, a varus/valgus selector 506, a coronal portion 508, a transverse portion 510, and a sagittal portion 512. The interface 500 also includes a virtual femur 514 that corresponds to the femur 206 and a virtual femoral implant 516 that corresponds to the femoral component of the implant being used in the procedure.

The user selection portion 502 allows the user to enter the name of the user into the user selection portion 502 such that changes made to any preferences can be saved to a profile associated with the user. Various user profiles can be stored within the computing system 224 and can be retrieved by the user entering the user name in the user selection portion 502. In some embodiments, the user selection portion includes a dropdown menu that allows the user to select the user name from a list of users. In some embodiments, to access the user preferences or the user profile associated with the user, a password or passcode must be entered via the input/output device 262. In embodiments where the input/output device 262 includes one or more biometric sensors (e.g., fingerprint scanner, retina scanner, facial recognition technology, etc.), the user may be identified and/or verified by one or more biometric data points.

The selection menu 504 provides a variety of selectable buttons that the user can select to change what is displayed on the display 246. In the example embodiment shown in FIG. 5, the user has selected the "femur planning" button, and therefore the interface 500 shows various elements related to planning a surgical procedure related to the femur. If the user selects the "tibia planning" button, the interface 500 would show various elements related to planning a surgical procedure related to the tibia. As shown, the varus/valgus selector allows the user to select either "varus" or "valgus" and then enter preferences according to the selection. In some embodiments, the user may be provided an option to duplicate the preferences entered. For example, the user may enter surgical preferences for a varus configuration, as shown in FIG. 5. If the user desires to have the same preferences for a valgus configuration, the user may be presented with a check box that can be selected to duplicate the user's preferences from the varus configuration.

The coronal portion 508, transverse portion 510, and sagittal portion 512 each provide the user with the ability to adjust surgical preferences specific to each particular view. As shown, each of the coronal portion 508, transverse portion 510, and sagittal portion 512 show the user a view of the virtual femur 514 and the virtual femoral implant 516 in the appropriate view from which the user can enter the surgical preferences. The user can enter or change surgical preferences by selecting the "+" or "−" buttons next to each of the numerical values shown such that the user defines a preference range for each surgical parameter. The user can also enter numbers directly in the boxes provided using the keyboard 266 instead of selecting the "+" or "−" buttons. For example, in the coronal portion 508 the user can enter preferred maximum and minimum coronal rotation value (e.g., a preferred coronal rotation range), preferred maximum and minimum medial distal resection values (e.g. preferred medial distal resection range), and preferred maximum and minimum lateral distal resection values (e.g., preferred lateral distal resection range). Similarly, in the transverse portion 510, the user can enter a preferred transverse rotation range, a preferred medial posterior resection range, and a preferred lateral posterior resection range. In the sagittal portion 512, the user can enter a preferred sagittal rotation range. After providing the user selections, the user can save the preference ranges by selecting the "save" button, or the user can cancel by selecting the "cancel" button. In some embodiments, in addition to the options presented to the user in the "femur planning" portion, the user may be presented with additional and/or other options in the "tibia planning" portion. For example, the "tibia planning" portion may provide the user the ability to set a posterior slope for both a cruciate retaining ("CR") implant and a posterior stabilizing ("PS") implant.

Figure 6:
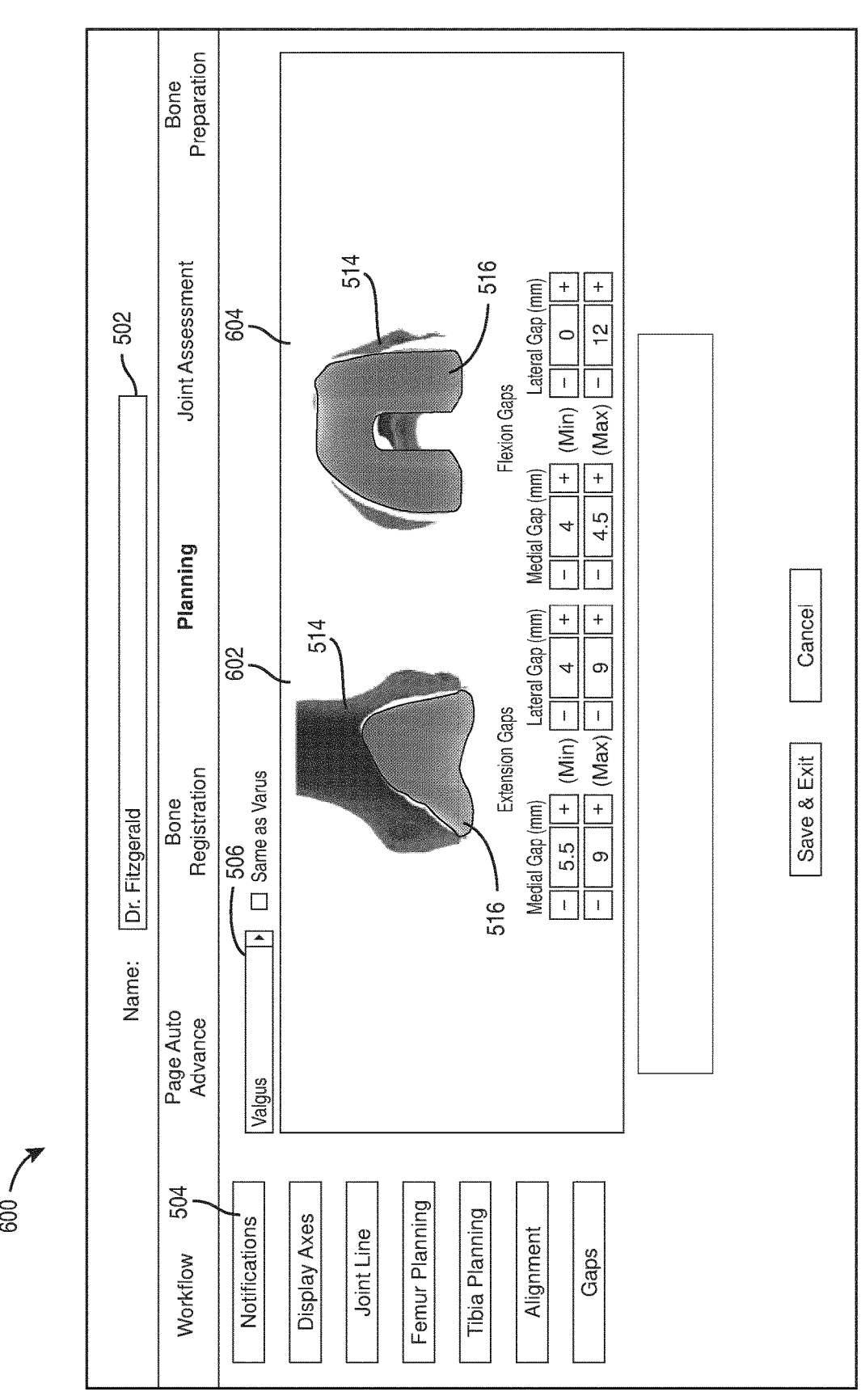
FIG. 6 is an illustration of another surgeon preference selection interface, according to an exemplary embodiment.

FIG. 6 is an illustration of another surgeon preference selection interface 600, according to an exemplary embodiment. In some embodiments, the surgeon preference selection interface 600 (e.g., "the interface 600") is displayed to a user via the display 246, and the user (e.g., a surgeon or other medical professional) can interact with the display 246 via the input/output device 262, which can include the keyboard 266 and a mouse (not shown). The interface 600 is shown to include the user selection portion 502, the selection menu 504, the varus/valgus selector 506, a flexion gap portion 604, and an extension gap portion 602. The interface 500 also includes the virtual femur 514 and the virtual femoral implant 516.

To navigate to the interface 600, the user selects the "gaps" button on the selection menu 504 such that the display 264 shows the interface 600. The flexion gap portion 604 and the extension gap portion 602 each provide the user with the ability to adjust surgical preferences specific to each particular view. As shown, each of the flexion gap portion 604 and the extension gap portion 602 show the user a view of the virtual femur 514 and the virtual femoral implant 516 in the appropriate view from which the user can enter the surgical preferences. The user can enter or change surgical preferences by selecting the "+" or "−" buttons next to each of the numerical values shown such that the user defines a preference range for each surgical parameter. The user can also enter numbers directly in the boxes provided using the keyboard 266 instead of selecting the "+" or "−" buttons. For example, in the extension gap portion 602 the user can enter a preferred maximum and minimum medial extension gap (e.g., a preferred medial extension gap range) and a preferred maximum and minimum lateral extension gap (e.g., a preferred lateral extension gap range). Similarly, in the flexion gap portion 604 the user can enter a preferred medial flexion gap range and preferred lateral flexion gap range. In some embodiments, the interface 600 allows the user to set different surgical preferences for the same attribute based on the type of implant being used. For example, the user can have a first set of gap preferences when the surgical procedure involves a CR implant and a second set of gap preferences when the surgical procedure involves a PS implant.

Figure 7:
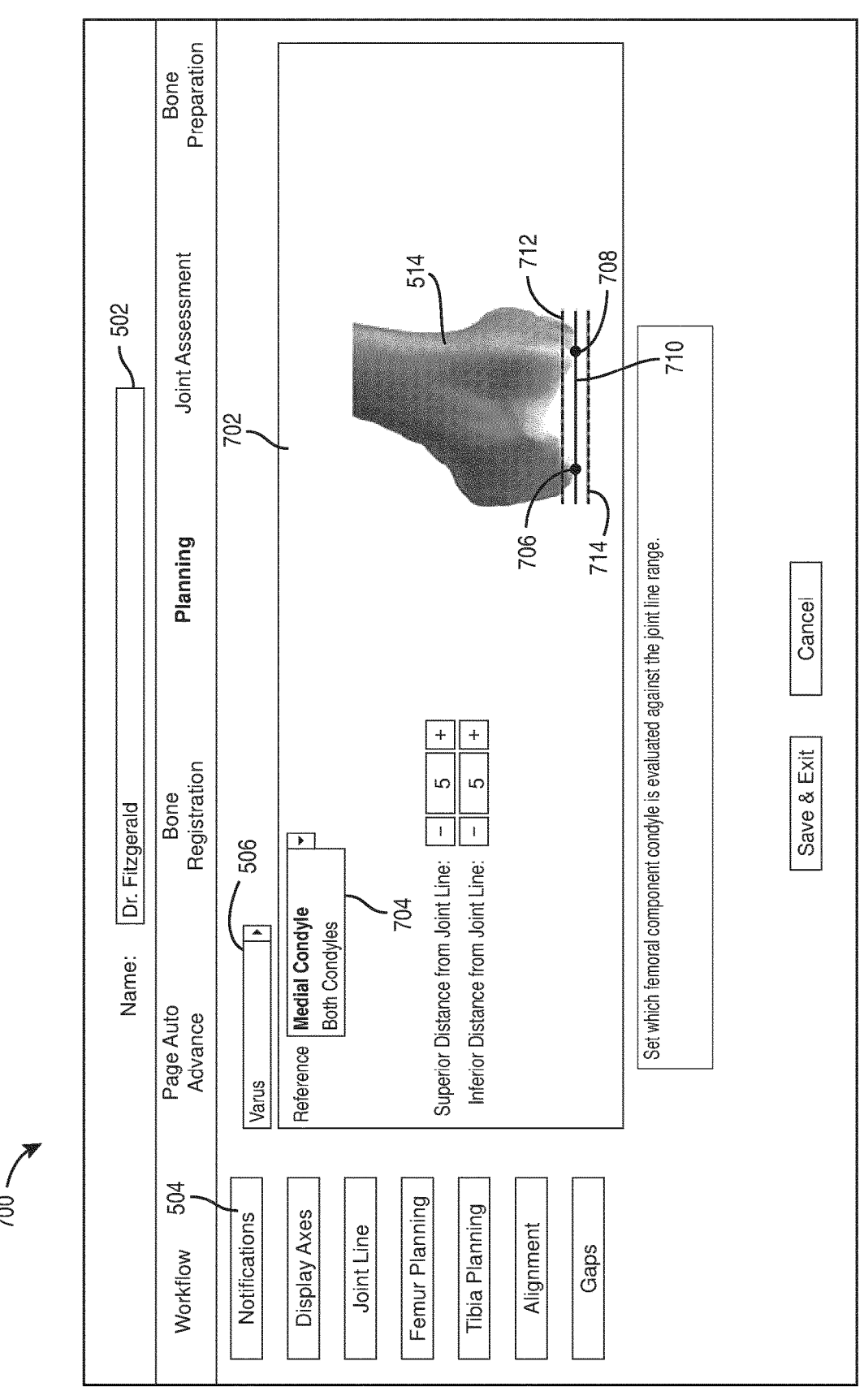
FIG. 7 is an illustration of yet another surgeon preference selection interface, according to an exemplary embodiment.

FIG. 7 is an illustration of yet another surgeon preference selection interface 700, according to an exemplary embodiment. In some embodiments, the surgeon preference selection interface 700 (e.g., "the interface 700") is displayed to a user via the display 246, and the user (e.g., a surgeon or other medical professional) can interact with the display 246 via the input/output device 262, which can include the keyboard 266 and a mouse. The interface 700 is shown to include the user selection portion 502, the selection menu 504, the varus/valgus selector 506, a joint line portion 702, and a reference selection portion 704. The interface 700 also includes the virtual femur 514.

The joint line portion 702 allows the user to select joint line preferences with respect to one or more condyles of the virtual femur 514. For example, the user can select a reference from the reference selection potion 704 to determine the reference point(s) from where the joint line is measured. The user can select the reference as the medial condyle, the lateral condyle, or both condyles. Upon selection of the reference, the computer device 224 determines the location of a joint line 710 (e.g., a mid-line of the joint)

and displays the joint line 710 on the interface 700. The joint line 710 extends between a first joint landmark 706 and a second joint landmark 708, where the first joint landmark 706 is located on a first condyle of the virtual femur 514 and the second joint landmark 708 is located on a second condyle of the virtual femur 514. A superior joint line 712 and an inferior joint line 714 are also displayed on the interface 700 and indicate the user's preference for acceptable positions of the joint line 710. For example, the user can adjust the distance between the superior joint line 712 and the joint line 710 by selecting the "+" or "−" buttons next to each of the numerical values corresponding to the superior joint line 712. The user can also adjust the distance between the inferior joint line 714 and the joint line 710 by selecting the "+" or "−" buttons next to each of the numerical values corresponding to the inferior joint line 714. Accordingly, the user defines a preferred joint line range which is bounded by the superior joint line 712 and the inferior joint line 714.

Figure 8:
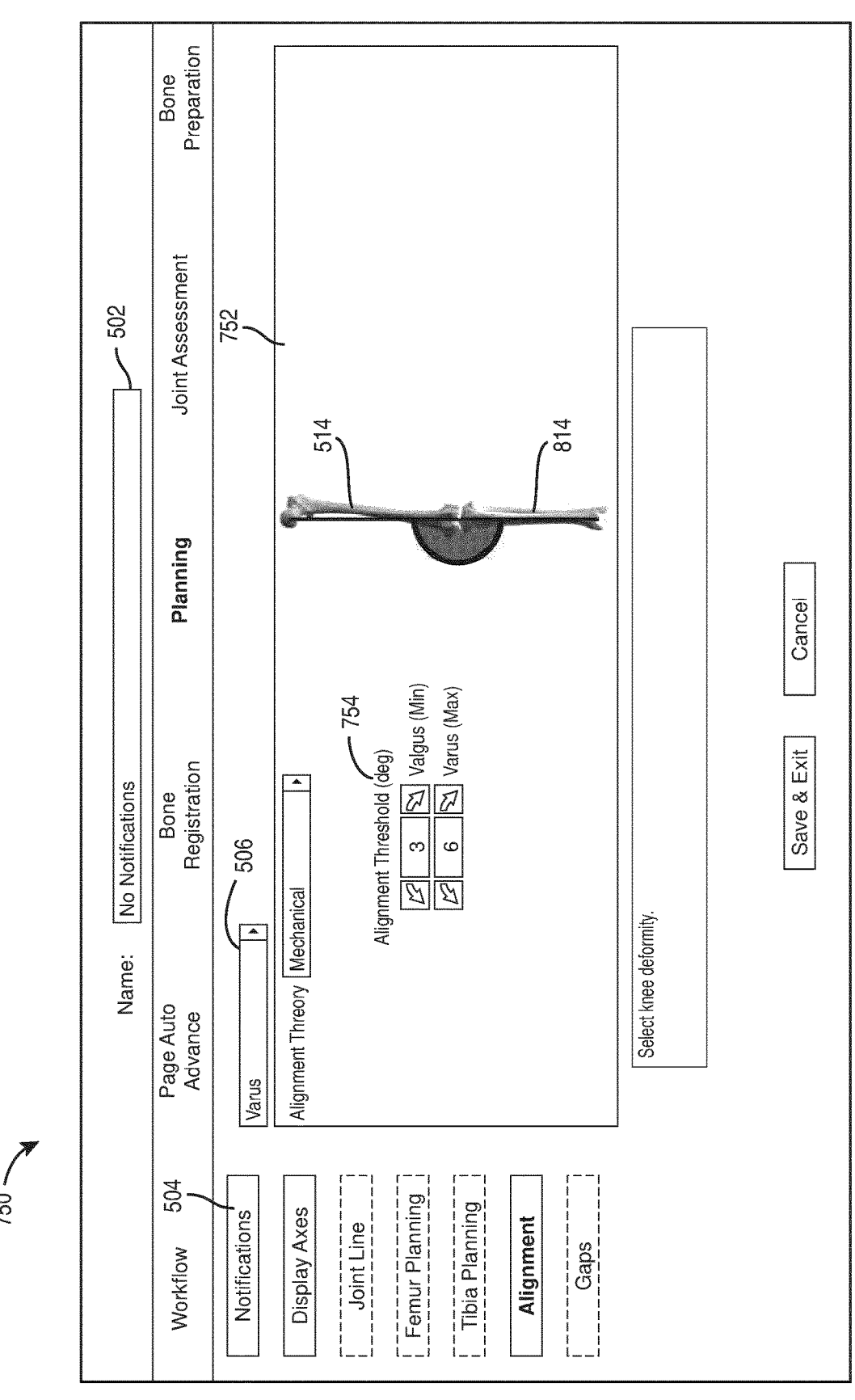
FIG. 8 is an illustration of yet another surgeon preference selection interface, according to an exemplary embodiment.

FIG. 8 is an illustration of yet another surgeon preference selection interface 750, according to an exemplary embodiment. In some embodiments, the surgeon preference selection interface 750 (e.g., "the interface 750") is displayed to a user via the display 246, and the user (e.g., a surgeon or other medical professional) can interact with the display 246 via the input/output device 262, which can include the keyboard 266 and a mouse. The interface 750 is shown to include the user selection portion 502, the selection menu 504, the varus/valgus selector 506, and an alignment portion 752. The alignment portion 752 includes an alignment threshold selector 754, a reference selection portion 704, the virtual femur 514, and the virtual tibia 814.

The alignment portion 752 allows the user to select varus/valgus alignment preferences with respect to the virtual femur 514 and the virtual tibia 814. For example, the user can select the desired varus/valgus alignment thresholds using the alignment threshold selector 754. To increase the allowable alignment threshold, the user selects the arrow to the right of the numeral to be increased. To decrease the allowable threshold, the user selects the arrow to the left of the numeral to be decreased. In the example embodiment shown, the user has selected a valgus threshold of three degrees and a varus threshold of six degrees. The values of the varus and valgus alignment thresholds depends on the user preferences and the type of procedure being planned.

Figure 9:
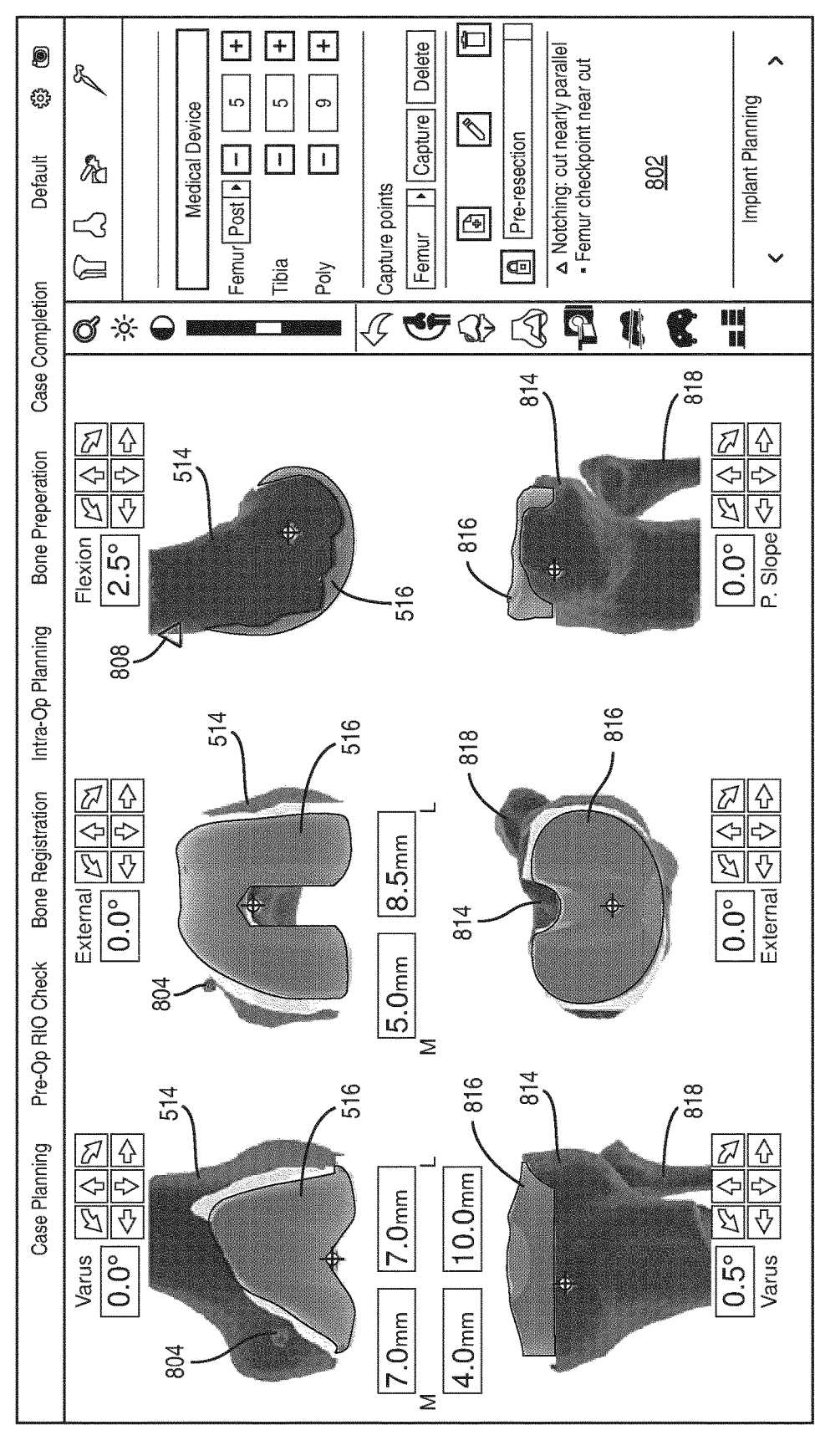
FIG. 9 is an illustration of a surgical planning interface providing warnings, according to an exemplary embodiment.

FIG. 9 is an illustration of a surgical planning interface 800 providing warnings, according to an exemplary embodiment. In some embodiments, the surgical planning interface 800 (e.g., "the interface 800") is displayed to a user via the display 246, and the user (e.g., a surgeon or other medical professional) can interact with the display 246 via the input/output device 262, which can include the keyboard 266 and a mouse (not shown). The interface 800 is shown to include a warning box 802, the virtual femur 514, and the virtual femoral implant 516. The interface 800 further includes a virtual tibia 814 corresponding to the tibia 208, a virtual tibial implant 816 corresponding to the implant being used in the surgical procedure, and a virtual fibula 818.

In some embodiments, the computer system 224 analyzes a planned surgical procedure to determine whether there are any issues that may prevent or hinder a successful procedure. If the computer system 224 determines that an issue exists, the computer system 224 communicates the issue to the user via a warning on the planning interface 800. For example, as shown in FIG. 8, the interface 800 includes a warning box 802 that provides one or more text warning to the user to notify the user of issues. As shown in the example embodiment of FIG. 9, the warning box 802 provides the warnings. "Notching: cut nearly parallel," and "Femur checkpoint near cut." Though not shown in FIG. 9, the warning box 802 may also provide the warning "Potential notch." The "Notching: cut nearly parallel" warning refers to a warning that a planned cut into the femur 206 is almost parallel to the surface of the femur 206. Planning cuts that are nearly parallel to the surface of the bone may present issues because cutting parallel to the bone is difficult and may result in a cut that is less accurate than desired, and may result in cutting a true notch in the bone. The "Potential notch" warning refers to a warning that, in addition to a planned cut that may result in a notch cut into the bone, additional surgical parameters may result in a notch cut into the bone. The "Femur checkpoint near cut" warning refers to a warning that a checkpoint (e.g., a physical reference point used by the computer system 224 during the procedure) is close to being hit by a cutting tool during a cut. Planning cuts that are near a checkpoint present may present issues because if a checkpoint hit by the cutting tool, both the cutting tool and the checkpoint may be damaged and/or moved, and the bone to which the checkpoint is coupled may be damaged as well. Furthermore, if a checkpoint is damaged and/or moved the computer system 224 loses a reference point from which other measurements were made, with no way to verify registrations of the damaged/moved checkpoint relative to other checkpoints. Therefore, the accuracy of the procedure is reduced. Though two warnings are shown in the warning box 802, the number of warnings in the warning box 802 can vary based on the number of issues detected by the computer system 224. Accordingly, the warning box 802 can display more or fewer warnings than shown in FIG. 8.

In some embodiments, the computer 224 determines whether to provide a checkpoint warning based on a distance between a checkpoint and a plane aligned with the planned cut. If the distance between the checkpoint and the plane is less than a threshold distance, the computer 224 provides a warning. In some embodiments, the computer 224 determines whether to provide a checkpoint warning based on a distance between a checkpoint and a virtual boundary of a haptic object planned for a cut. If the distance between the checkpoint and the virtual boundary is less than a threshold distance, the computer 224 provides a warning.

In addition to the text warnings provided in the warning box 802, the text warnings are associated with specific symbols that represent those warnings. As shown in the example embodiment of FIG. 9, the "cut nearly parallel" warning is associated with a triangle, and the "checkpoint near cut" warning is associated with a circle or dot. Though certain symbols are shown as being associated with certain warnings in FIG. 9, in various embodiments other symbols can be associated with those warnings. Also as shown in the example embodiment of FIG. 9, the symbols associated with the warnings are displayed on the virtual femur 514 and/or the virtual femoral implant 516 on the interface 800. Furthermore, the symbols associated with the warnings are displayed on virtual femur 514 and/or the virtual femoral implant 516 in the locations at which the issues exist. For example, a checkpoint warning symbol 804 is shown on the virtual femur 514 in both the varus view and the external view on the interface 800. In addition, a notching warning symbol 808 is shown on the virtual femur 514 in the flexion view. Displaying the warning symbols directly on the virtual femur 514 and/or the virtual femoral implant 516 provides the user with additional context of the warnings such that the user can determine exactly where the issue exists and begin to address the issue.

In some embodiments, the text in the warning box 802 is selectable, and upon the user selecting one of the warnings displayed in the warning box 802, the corresponding warning symbol(s) on the interface 800 will be emphasized (e.g., bolded, italicized, highlighted, change color, or otherwise emphasized such that it is displayed in a fashion different from how it was displayed prior to the user selecting the warning text). For example, if the user selects the checkpoint warning text in the warning box 802 (e.g., by selecting the text using the input/output device 262), the checkpoint warning symbol 804 may be emphasized based on the selection. In some embodiments, the checkpoint warning symbol 804 may become larger, change color, flash, or otherwise be emphasized based on the selection of the corresponding warning in the warning box 802.

Figure 10:
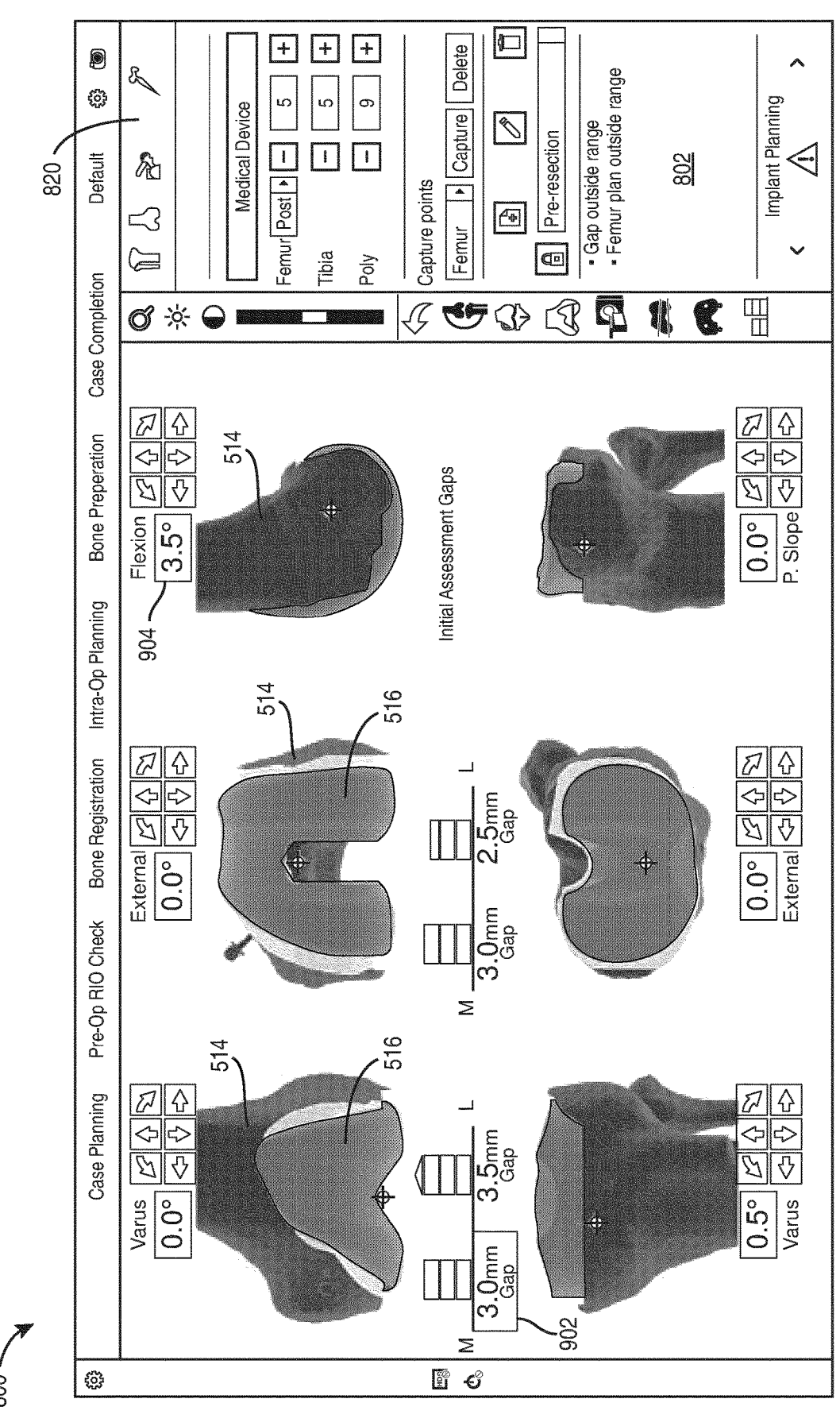
FIG. 10 is an illustration of the surgical planning interface of FIG. 9 providing additional warnings, according to an exemplary embodiment.

FIG. 10 is an illustration of the surgical planning interface 800 of FIG. 9 providing additional warnings, according to an exemplary embodiment. As shown in the example embodiment in FIG. 10, the warning box 802 provides the warnings "Gap outside range," and "Femur plan outside range." The "Gap outside range" warning refers to a warning that a gap between the virtual femur 514 and the virtual femoral implant 516 is outside of the preferred range defined by the user (e.g., in FIG. 5-7). Having a gap that is larger than desired may result in instability between the femur 206 and the tibia 208. The "Femur plan outside range" warning refers to a warning that another parameter of the surgical plan (e.g., parameters other than a planned gap, e.g., a planned flexion angle, etc.) is outside of the preferred range defined by the user. Having such parameters outside of the preferred range may also result in various other issues. For example, the implant may be cut more than required, which may allow for too much movement and/or angular instability within the joint. In addition, the implant may be placed outside the clinically acceptable range. Though two warnings are shown in the warning box 802, one of skill in the art would understand that the number of warnings in the warning box 802 depends on the number of issues detected by the computer system 224. Accordingly, the warning box 802 can display more or fewer warnings than shown in FIG. 10. In some embodiments, the warning box 802 can display both surgical warnings (e.g., warnings that would indicate when the surgical procedure may be unsuccessful) and warnings based on a surgeon preference (e.g., warnings that an aspect of the procedure is outside of the surgeon's preferences, but does not necessarily indicate that the surgical procedure may be unsuccessful). In such embodiments, the warnings based on surgeon preference may be toggled on and off, but the surgical warnings cannot be toggled on and off (e.g., the surgical warnings are always displayed).

In addition to the text warnings provided in the warning portion 802, the text warnings may be associated with specific symbols that represent those warnings. As shown in the example embodiment of FIG. 10, the "gap outside range" warning is associated with a warning indicator 902, which is shown as a box around the medial gap indicated in the varus portion of the interface 800. Though shown as a box in FIG. 10, in some embodiments the warning indicator 902 can be any type of indicator that emphasizes the specific parameter that is outside the preferred range indicated by the user (e.g., the parameter may be circled, highlighted, change color, blink, etc.). Furthermore, though the warning is shown in the varus portion of the interface 800, the warning can be shown on any view (e.g., coronal view, transverse view, etc.). The "femur plan outside range" warning is associated with a warning indicator 904. The warning indicator 904 is shown as a box around the flexion parameter. Similar to the warning indicator 902, in some embodiments the warning indicator 904 can be any type of indicator that emphasizes the specific parameter that is outside the preferred range indicated by the user (e.g., the parameter may be circled, highlighted, change color, blink, etc.).

As described, in some embodiments, the text in the warning box 802 is selectable, and upon the user selecting one of the warnings displayed in the warning box 802, the corresponding warning symbol(s) on the interface 800 will be emphasized (e.g., bolded, italicized, highlighted, change color, or otherwise emphasized such that it is displayed in a fashion different from how it was displayed prior to the user selecting the warning text). For example, if the user selects the "gap outside range" warning text in the warning box 802 (e.g., by selecting the text using the input/output device 262), the warning indicator 902 may be emphasized based on the selection. In some embodiments, the warning indicator 902 may become larger, change color, flash, or otherwise be emphasized based on the selection of the corresponding warning in the warning box 802.

Figure 11:
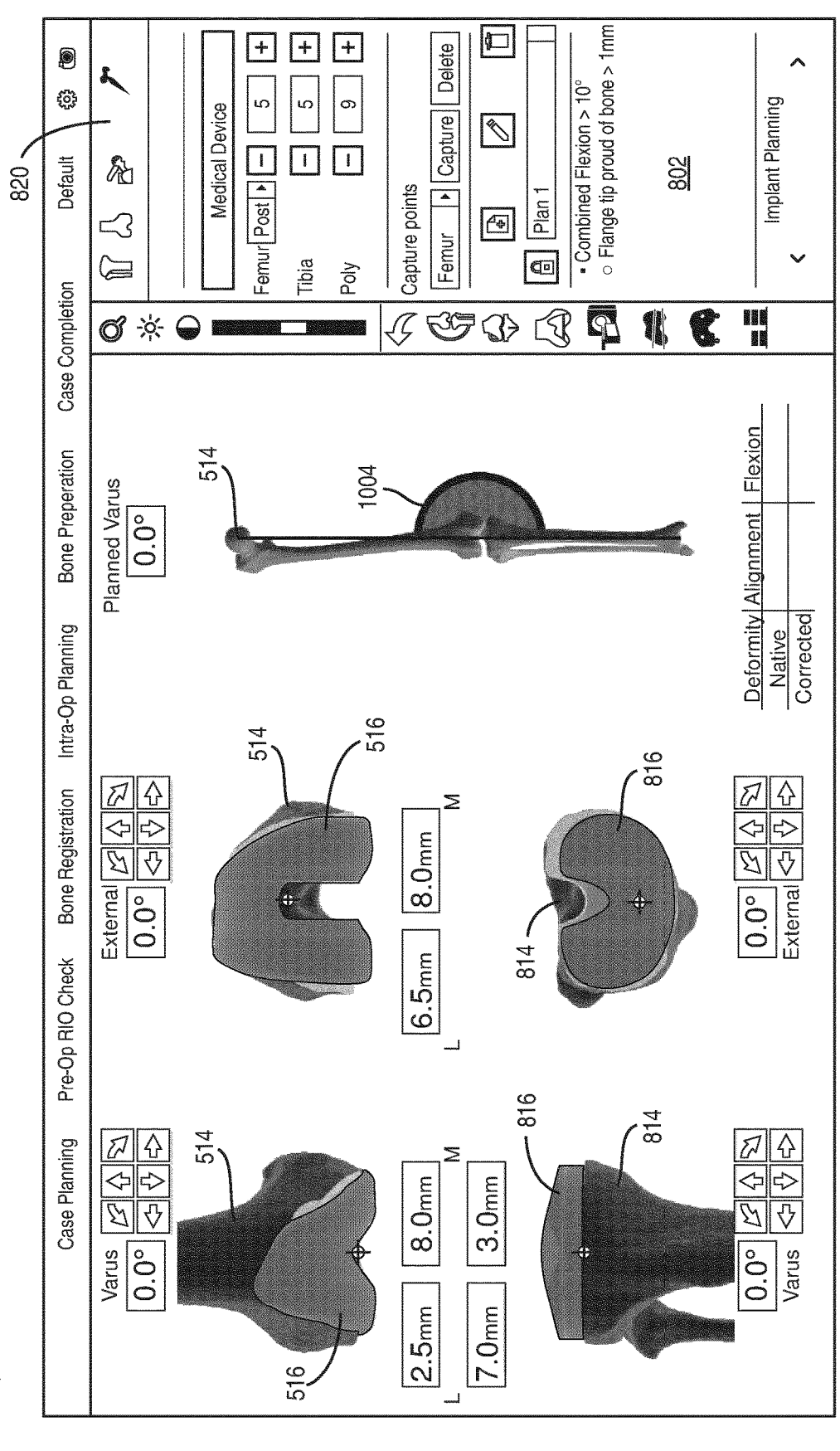
FIG. 11 is an illustration of another embodiment of the surgical planning interface of FIG. 9 providing further warnings, according to an exemplary embodiment.

FIG. 11 is an illustration of another embodiment of the surgical planning interface 800 of FIG. 9 providing further warnings, according to an exemplary embodiment. As shown in the example embodiment in FIG. 11, the warning box 802 provides the warnings "Combined flexion >10°," and "Flange tip proud of bone >1 mm." The "Combined flexion" and "Flange tip proud of bone warnings are further discussed with reference to FIG. 12.

In addition to the text warnings provided in the warning portion 802, the text warnings are associated with specific symbols or indicators that represent those warnings. As shown in the example embodiment of FIG. 11, the "combined flexion" warning is associated with an combined flexion warning 1004 that emphasizes the flexion of the virtual tibia 814 relative to the virtual femur 514. In some embodiments, the combined flexion warning 1004 includes additional or other indications to emphasize the combined flexion issue (e.g., a change in pattern, blinking, flashing, enlarging, etc.).

In some embodiments, the text in the warning box 802 is selectable, and upon the user selecting one of the warnings displayed in the warning box 802, the corresponding warning symbol(s) on the interface 800 will be emphasized (e.g., bolded, italicized, highlighted, change color, or otherwise emphasized such that it is displayed in a fashion different from how it was displayed prior to the user selecting the warning text). For example, if the user selects the combined flexion warning text in the warning box 802 (e.g., by selecting the text using the input/output device 262), a combined flexion warning 1004 and/or a flange tip proud of bone warning on the interface 800 may be emphasized based on the selection. In some embodiments, the warnings may become larger, change color, flash, or otherwise be emphasized based on the selection of the corresponding warning in the warning box 802.

Figure 12:
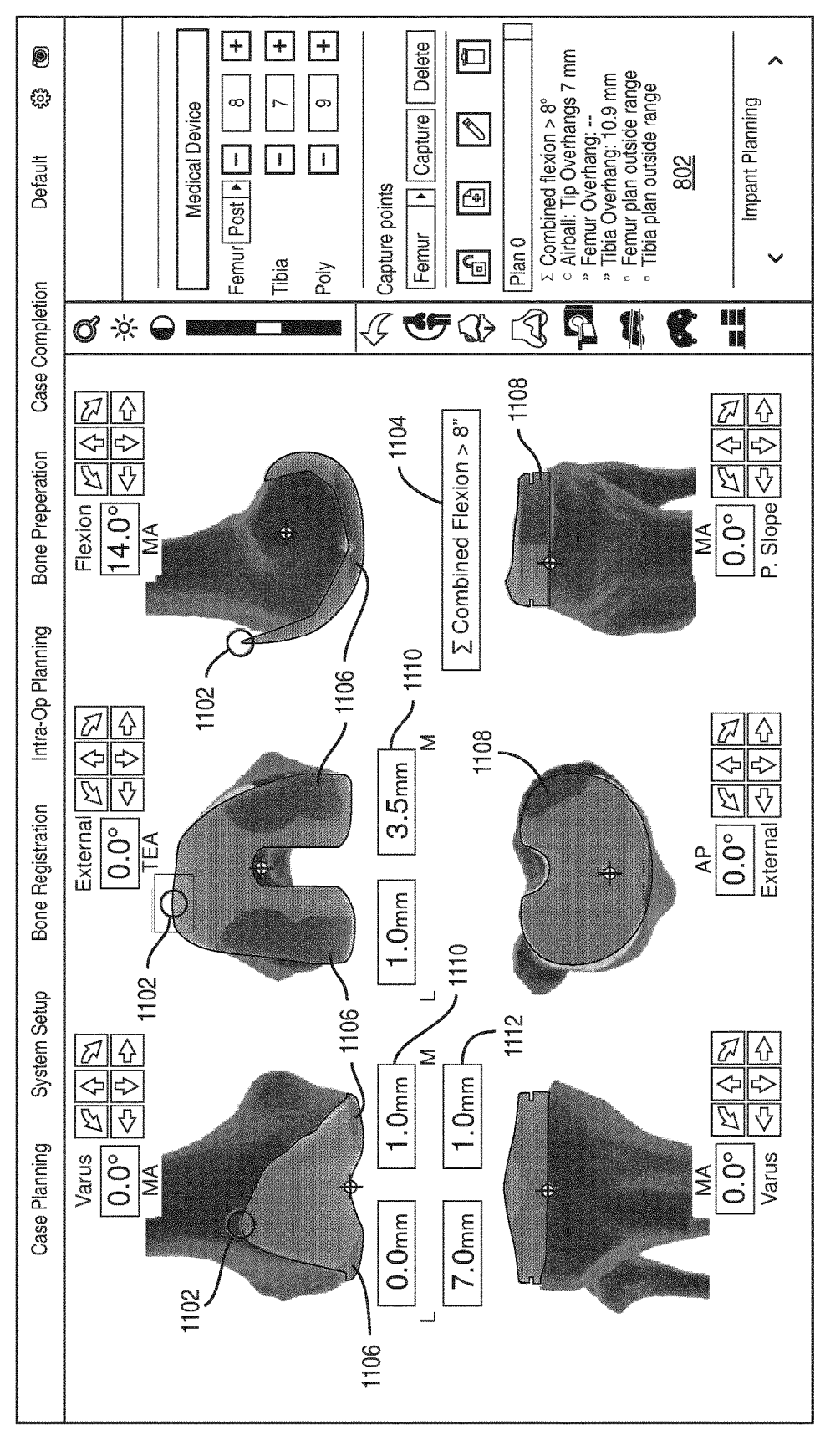
FIG. 12 is an illustration of another embodiment of the surgical planning interface of FIG. 9 providing more warnings, according to an exemplary embodiment.

FIG. 12 is an illustration of another embodiment of the surgical planning interface 800 of FIG. 9 providing more warnings, according to an exemplary embodiment. As discussed with reference to FIGS. 9-11, in some embodiments the warning box 802 displays text corresponding to a warning displayed with a symbol shown on the virtual femur 514, the virtual tibia 814, the virtual femoral implant 516, the virtual tibial implant 816, or elsewhere on the interface 800 to indicate the exact location of the issue. In some embodiments, and as shown in FIG. 11, the warnings provided in the warning box 802 may also include symbols that correspond to the symbols provided in the exact locations of the issues.

For example, the warning box 802 includes a "combined flexion" warning (similar to the "combined flexion" warning of FIG. 11) that indicates the combined flexion (e.g., the combined flexion between the virtual femur 514 and the virtual tibia 814) is greater than eight degrees, which is outside of the clinically acceptable range. Though eight degrees was used for illustrative purposes, one of skill in the art would understand that the clinically acceptable range may be any preset number based on the presentation of the patient undergoing the surgical procedure. Having the combined flexion outside of the preferred range of the user may cause problems when attempting to perform the surgical procedure as the joint may exhibit intercomponent implant impingement. As shown in the warning box 802, the "combined flexion" warning may also include the Greek letter Σ. The Greek letter Σ may also be included in a combined flexion warning 1104, shown on the interface 800 in the flexion portion. Providing the same symbol (e.g., the Greek letter Σ, or another symbol that can be associated with the combined flexion warning) in both the warning box 802 and the combined flexion warning 1104 provides continuity to the user when analyzing the potential issues, as the user may view the symbol associated with the warning in the warning box and then attempt to find the same symbol on the virtual components to determine exactly where the issue lies. In some embodiments, as described above, the user may select the "combined flexion" warning in the warning box 802 to cause the combined flexion warning 1104 to be emphasized on the interface 800 such that the user can easily locate the warning.

As another example, the warning box 802 includes an "airball: tip overhang" warning that indicates the tip of an implant component (e.g., the virtual femoral implant 516) overhangs a bone (e.g., the virtual femur 514). In some embodiments, the "airball: tip overhang" warning is equivalent to the "flange tip proud of bone" warning described in FIG. 10. Accordingly, descriptions of the "airball: tip overhang" warning provided herein are also applicable to the "flange tip proud of bone warning." The "airball: tip overhang" warning may also include an amount (e.g., a numeric value) by which the implant component is overhanging (e.g., 7 millimeters (mm) in the example embodiment shown). The "airball: tip overhang" warning also includes an open circle symbol, which is also included in an airball warning 1102 shown on the virtual femoral implant 516 on the interface 800 in the varus (coronal), external (transverse), and flexion (saggital) portions. Providing the same symbol (e.g., the open circle symbol) in both the warning box 802 and the airball warning 1102 provides continuity to the user when analyzing potential issues, as the user may view the symbol associated with the warning in the warning box and then attempt to find the same symbol on the virtual components to determine exactly where the issue lies. In some embodiments, as described above, the user may select the "airball" warning in the warning box 802 to cause the airball warning 1102 to be emphasized on the interface 800 such that the user can easily locate the warning.

As yet another example, the warning box 802 includes a "femur overhang" warning and a "tibia overhang" warning. As described, an overhang warning provides the user a warning when the virtual implant (and, therefore, the planned position of the actual implant) extends beyond a boundary (e.g. a perimeter) of the virtual bone. An implant that overhangs a bone may interfere with other internal structures such as soft tissue, thereby decreasing the effectiveness of the procedure. The "overhang" warning in the warning box 802 also includes an overhang symbol and, in some embodiments, may include an amount by which the implant overhangs the bone. In some embodiments, the overhang symbol may also be provided on the interface 800 at the particular locations of overhang. In some embodiments, and as shown in FIG. 12, the portions of the virtual implants that overhang the bone are sufficiently large such that the overhanging portions are emphasized in another manner (e.g., highlighting, etc.) to avoid a plurality of overhang symbols overlapping each other and causing confusion for the user. For example, portions of the virtual femoral implant 516 overhanging the virtual femur 514 are indicated by a femoral overhang indicator 1106. Portions of the virtual tibial implant 816 that overhang the virtual tibia 814 are indicated by a tibial overhang indicator 1108.

Furthermore, the warning box 802 includes a "femur plan outside range" warning and a "tibia plan outside range" warning. As described, these warnings refer to parameters that are outside the preferred ranges as defined by the user. The "outside range" warning in the warning box 802 also includes a box symbol adjacent to the warning. In some embodiments, the box symbol may also be provided on the interface 800 to emphasize the particular parameters that are outside of the preferred range of the user. In some embodiments, and as shown in FIG. 12, the "femur plan outside range" warning is associated with a femur plan outside range indicator 1110, shown on FIG. 12 as a box that surrounds the specific parameter that is outside the preferred range as defined by the user. As shown in FIG. 12, all of the femoral parameters are shown to be outside of the preferred range of the user. However, one of skill in the art would understand that, in some embodiments only a portion of the femoral parameters may be outside of the preferred range (and therefore emphasized by the femur plan outside range indicator 1110). Furthermore, though a box is shown as the femur plan outside range indicator 1110, any other type of indicator may be used. In addition, though the word "plan" is shown as being part of the warning, the warning may comprise wording that is more specific. For instance, if the resection of the femur 206 is outside the range, the warning box 802 may include a warning that indicates "femur resection outside range." In addition, if the rotation of the femur 206 is outside the range, the warning box 802 may include a warning that indicates "femur rotation outside of range."

In some embodiments, and also as shown in FIG. 12, the "tibia plan outside range" warning is associated with a tibia plan outside range indicator 1112, shown on FIG. 12 as a box that surrounds the specific parameter that is outside the preferred range as defined by the user. As shown in FIG. 12, all of the tibial parameters are shown to be outside of the preferred range of the user. However, one of skill in the art would understand that, in some embodiments only a portion of the tibial parameters may be outside of the preferred range (and therefore emphasized by the tibia plan outside range indicator 1112). Furthermore, though a box is shown as the tibia plan outside range indicator 1112, any other type of indicator may be used.

In any of the embodiments described with reference to FIGS. 9-12, when the user selects a specific warning the user may be presented with options to correct the warning. In some embodiments, the computer system 224 may present the user with options to correct the warning by either 1) changing the preferred ranges selected by the user or 2) changing the surgical plan. The user may be able to select which option by selecting a button corresponding to the desired option on the interface 800. Upon selecting the desired option, the computer system 224 directs the user to the appropriate interface to make the desired changes.

FIG. 13 is an illustration of a table 1200 showing various symbols that correspond to warnings, according to an exemplary embodiment. The symbols shown in the table 1200 are displayed on a user interface (e.g., the interface 800) to indicate a specific location of the warnings, as described above with respect to FIGS. 9-12. Though specific symbols are shown in FIG. 13, different or modified symbols may be implemented in other embodiments. In some embodiments, some warnings may be associated with certain symbols and some warnings may not be associated with any symbols (e.g., only text warnings are provided). Various warnings provided in FIG. 13 correspond to warnings already discussed with reference to FIGS. 9-12. Those warnings include notching, airballing, checkpoint, combined flexion, joint line, outside planning limits, gap threshold, and overhang. Those warnings not previously mentioned are discussed below.

A size mismatch warning is displayed when one of the implant components is much bigger or smaller than another of the implant components. Referring to the example of a knee replacement above, which includes a femoral implant and a tibial implant, a size mismatch warning will be displayed when the sizes of the virtual femoral implant 516 and the virtual tibial implant 816 differ by more than a threshold amount. Planning for implant components that are significantly different in size can cause complications during and after a procedure, as the components may not be compatible and may not fit together properly.

A captured points warning is displayed when the computer system 224 captures more than a threshold number of points (e.g., greater than 100 points), for example points associated with use of a tracked probe in a registration process. Capturing more than a threshold number of points can cause errors in planning in some scenarios. For example, capturing more than a threshold number of points can slow the performance of the surgical system. In an example embodiment, a clinically practical range of the limit of the threshold number of points is between sixty and one hundred sixty points. In another example embodiment, a clinically practical range of the limit of the threshold number of points is between eighty and one hundred twenty points. In yet another example embodiment, a clinically practical limit of the threshold number of points is one hundred points.

A floating bone warning is displayed when the virtual implant is moved proud (e.g., spatially offset) from an existing cut in the bone. Planning for an implant to be proud of an existing cut would cause the implant to not be in contact with the surface revealed by the existing cut in the bone if placed in such a position. Such a plan would therefore not allow for successful mounting of the implant on the bone, leading to complications during and after the surgical procedure.

Figure 14:
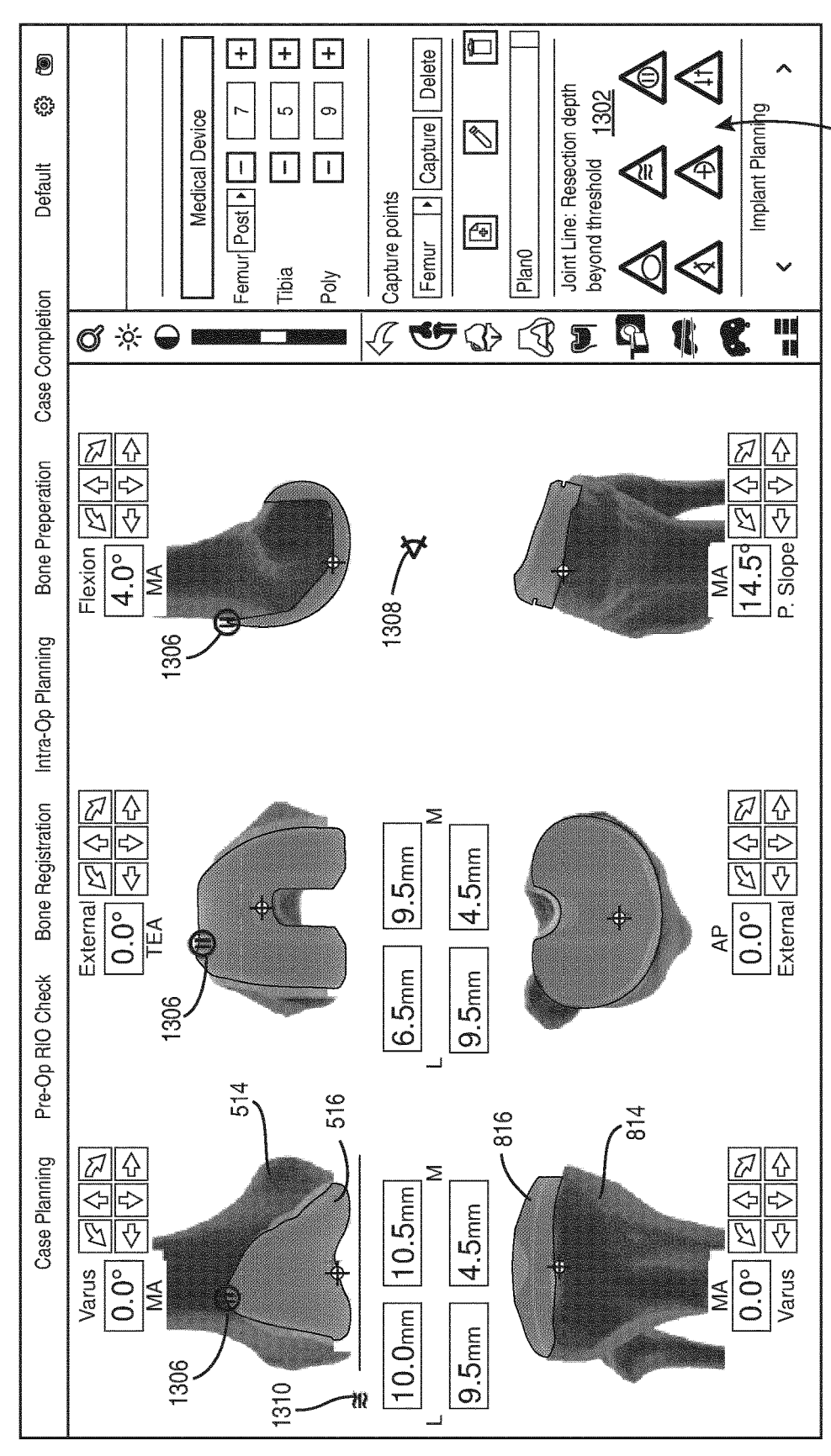
FIG. 14 is an illustration of another surgical planning interface providing selectable warnings, according to an exemplary embodiment.

FIG. 14 is an illustration of another surgical planning interface 1300 providing selectable warnings, according to an exemplary embodiment. In some embodiments, the surgical planning interface 1300 (e.g., "the interface 1300") is displayed to a user via the display 246, and the user (e.g., a surgeon or other medical professional) can interact with the display 246 via the input/output device 262, which can include the keyboard 266 and a mouse (not shown). The interface 1300 is shown to include a warning box 1302 that includes warning symbols 1304. The interface 1300 also shows the virtual femur 514, the virtual femoral implant 516, the virtual tibia 814, and the virtual tibial implant 816.

The warning box 1302 is similar to the warning box 802 described with reference to FIGS. 9-12; however, the warning box 1302 includes the warning symbols 1304, which are selectable icons or symbols that correspond to warnings generated by the computing system 224. The warning box 1302 allows the user to select a symbol displayed in the warning box 1302 and, upon selection of a symbol, text corresponding to the symbol is also displayed in the warning box 1302. For example, as shown in FIG. 14, the user selected the joint line warning symbol, and the text displayed in the warning box 1302 indicates "resection depth beyond threshold" (e.g., a planned cut extends beyond the preferred range as defined by the user). The user can select any of the symbols in the warning box 1302 to read the text warning associated with the symbol. In some embodiments, the position of the selectable symbols within the warning box 1302 remains constant. For example, a symbol positioned in the lower, right-hand corner of the warning box 1302 will always be in the same position regardless of whether there is a warning associated with the symbol. In some embodiments, the symbol is only displayed when there is a warning associated with the symbol. In such embodiments, when there is no warning associated with the symbol, the symbol is not displayed in the warning box 1302 (e.g., there is an empty space where the symbol would be displayed if there is an associated warning).

Furthermore, upon selection of the symbol by the user, a corresponding symbol on the interface 1300 located on or near the virtual femur 206 and/or the virtual tibia 208 is emphasized such that the user can view a precise physical location associated with the warning. For example, upon selecting the joint line warning symbol in the warning box 1302, a joint line warning 1310 is emphasized to the user on the interface 1300 such that the user can view the issue. In some embodiments, the joint line warning 1310 is emphasized by being highlighted, having a box form around it, changing color, becoming larger, or any other way in which the line joint warning may be emphasized to draw the attention of the user.

In addition to the joint line warning 1310, FIG. 14 shows a parallel cut warning 1306 and a flexion angle warning 1308. Accordingly, upon selection of the parallel cut warning symbol or the flexion angle warning symbol by the user in the warning box 1302, the corresponding warning symbol (e.g., the parallel cut warning 1306 or the flexion angle warning 1308) will be emphasized on the interface 1300.

Figure 15:
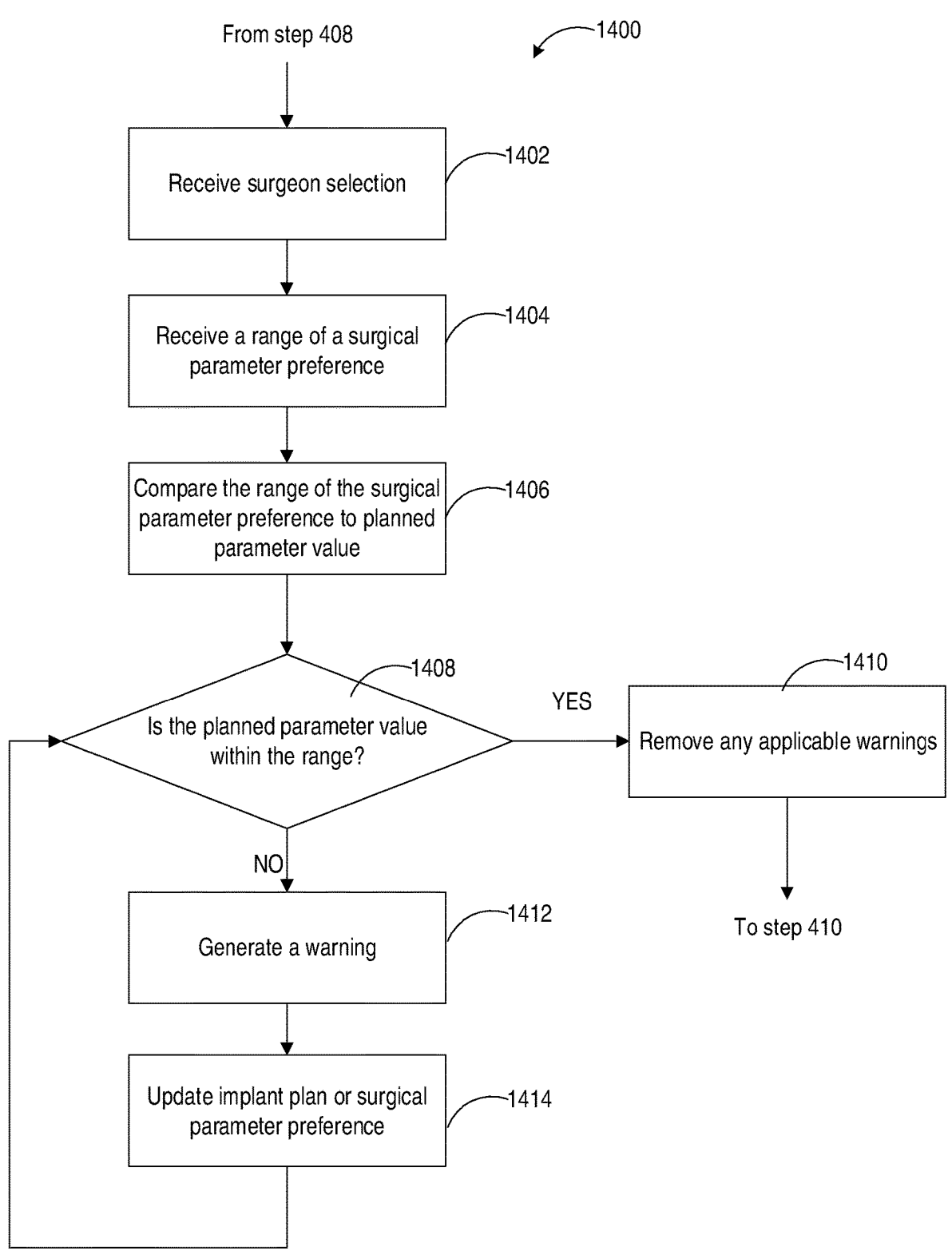
FIG. 15 is a flowchart of a process to generate warnings during an implant planning process, according to an exemplary embodiment.

FIG. 15 is a flowchart of a process 1400 to generate warnings during an implant planning process, according to an exemplary embodiment. The steps described in reference to the process 1400 can be executed by, for example, the computing system 224.

At step 1402, a surgeon selection is received. As described with reference to FIG. 9, a user selects, via the interface 800, which user (e.g., surgeon, physician, or other medical professional) is making selections to provide preferred ranges of parameters for a surgical procedure.

At step 1404, ranges of surgical parameter preferences are received. As described with reference to FIG. 9, the user selects, via the interface 800, various preferred ranges of parameters for a surgical procedure. The user can save the preferences such that the preferences can be referenced and accessed by the computing system 224 in response to a selection of that user in step 1402, for example. The user can change or modify preferences at any time via the interface 800.

At step 1406, the preferred parameter ranges are compared to the planned procedure. For example, the computing system 224 compares the parameters as planned during a procedure planning process to the preferred ranges as defined by the user.

At step 1408, a determination is made as to whether the planned parameter is within the preferred range. For example, the computing system determines, for each parameter, whether the planned parameter is within the preferred range as defined by the user, or if it is outside the preferred range. If the planned parameters are within the preferred ranges (YES at step 1408), then any warnings related to the preferred ranges that were previously displayed are removed at step 1410 and the surgical planning process can continue.

If any of the planned parameters are outside of the preferred ranges (NO at step 1408), then a warning is generated at step 1412. For example, a warning similar to those described with reference to FIGS. 9-12 and FIG. 14 is displayed to the user. In some embodiments, and in addition to the warning provided, the computing system 224 may provide guidance to the user as to how to address the warning and correct it. For example, if there is an overhang warning, the computing system 224 may provide a message to the user via the interface 800 or 1300 to show the user what parameters should be changed, and the value of the changes, to remove the warning. In some embodiments, the message from the computing system 224 may be in the form of text displayed on the interface 800 or 1300, but the message may also be audial (e.g., a voice telling the user how to correct for the warning).

At step 1414, the user can update the implant or the surgical parameter preference. For example, the user may determine that the preferences should not be changed, and therefore may update the surgical plan to eliminate the warnings found by the computing system 224. In some embodiments, the user may determine that the surgical parameter preferences should be changed to address the warnings. In such embodiments, the user can change the surgical parameter preferences as described with reference to step 1404. The computing system then again determines if the changes have placed the planned parameter values within the preferred range at step 1408 and, if so, the warnings are removed at step 1410 and the surgical planning process can continue.

Figure 16:
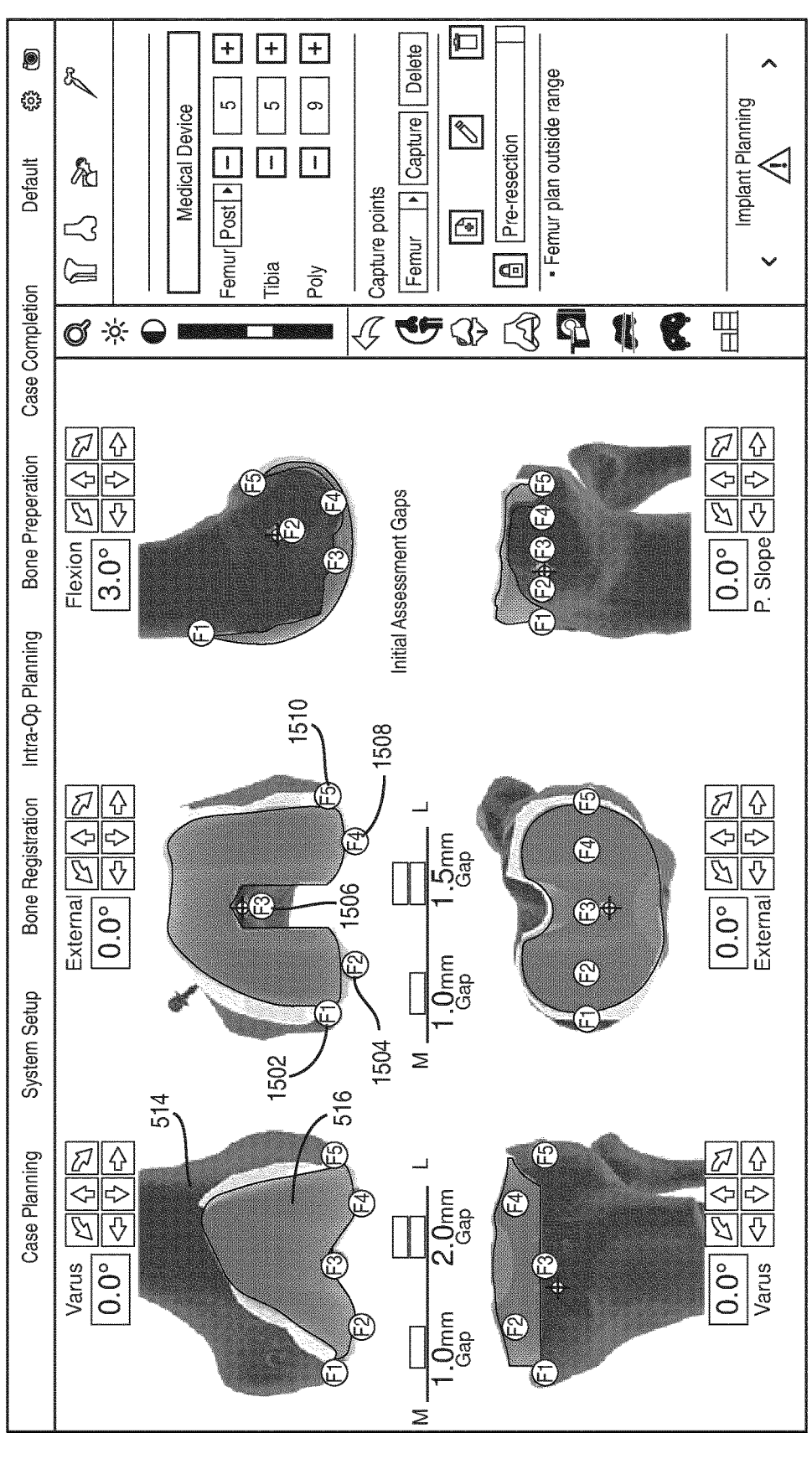
FIG. 16 is an illustration of an interface including preset anchor points, according to an exemplary embodiment.

FIG. 16 is an illustration of an interface 1500 including preset anchor points, according to an exemplary embodiment. As shown, the interface 1500 includes the virtual femur 514 and the virtual femoral implant 516. The interface 1500 is also shown to include a first preset anchor point 1502, a second preset anchor point 1504, a third preset anchor point 1506, a fourth preset anchor point 1508, and a fifth preset anchor point 1510. As described herein, the first preset anchor point 1502, the second preset anchor point 1504, the third preset anchor point 1506, the fourth preset anchor point 1508, and the fifth preset anchor point 1510 are referred to as "the preset anchor points 1502-1510." In some embodiments, the preset anchor points 1502-1510 correspond to specific geometric points on the virtual femoral implant 516. In some embodiments, the preset anchor points 1502-1510 correspond to specific bony landmarks on the virtual femur 514. In some embodiments, the preset anchor points 1502-1510 are generic landmarks that can be applied to any patient. In some embodiments, the preset anchor points 1502-1510 are landmarks that are specific to a particular patient.

In some embodiments, the preset anchor points 1502-1510 are associated with specific keys on the input/output device 262 (e.g., "hotkeys"). For example, the first preset anchor point 1502 may be associated with the "F1" key, the second preset anchor point 1504 may be associated with the "F2" key, the third preset anchor point 1506 may be associated with the "F3" key, the fourth preset anchor point 1508 may be associated with the "F4" key, and the fifth preset anchor point 1510 may be associated with the "F5" key. In some embodiments, the keys associated with the preset anchor points 1502-1510 are positioned on each respective preset anchor point on the interface 1500 to provide an indication (e.g., a "hotkey indicator" to the user which key is associated with which preset anchor point. In some embodiments, the preset anchor point scheme is consistent such that the user can quickly move between preset anchor points as desired. For example, the first preset anchor point 1502 (e.g., the most medial anchor point) may always be associated with the "F1" key, the last preset anchor point 1504 (e.g., the most lateral anchor point) may always be associated with the "F5" key, etc. One of skill will understand that the keys provided are examples, and the preset anchor points 1502-1510 may be associated with any number of possible keys or other inputs available via the input/output device 262.

The preset anchor points 1502-1510 allow the user to rotate the implant about the chosen anchor point to adjust the position of the implant during surgical planning. For example, if the user determines that the virtual femoral implant 516 is out of position and must be rotated about the first preset anchor point 1502, the user would select the first preset anchor point 1502 by selecting the key "F1" via the input/output device 262, and the user could then manipulate the virtual femoral implant 516 to achieve the desired orientation.

Using the preset anchor points 1502-1510 as described is advantageous because the preset anchor points 1502-1510 are defined based on physical landmarks (on the virtual femoral implant 516, the virtual femur 514, or both) so the user understands around which landmark the virtual femoral implant 516 is being rotated and advantageous symmetry or axes of rotation are provided. In contrast, in embodiments where the user can select any point around which to rotate, the user may rotate around an undesirable point without realizing it and have to correct for the undesirable rotation. Efficiency, usability, and accuracy of implant planning can thus be improved.

Figure 17:
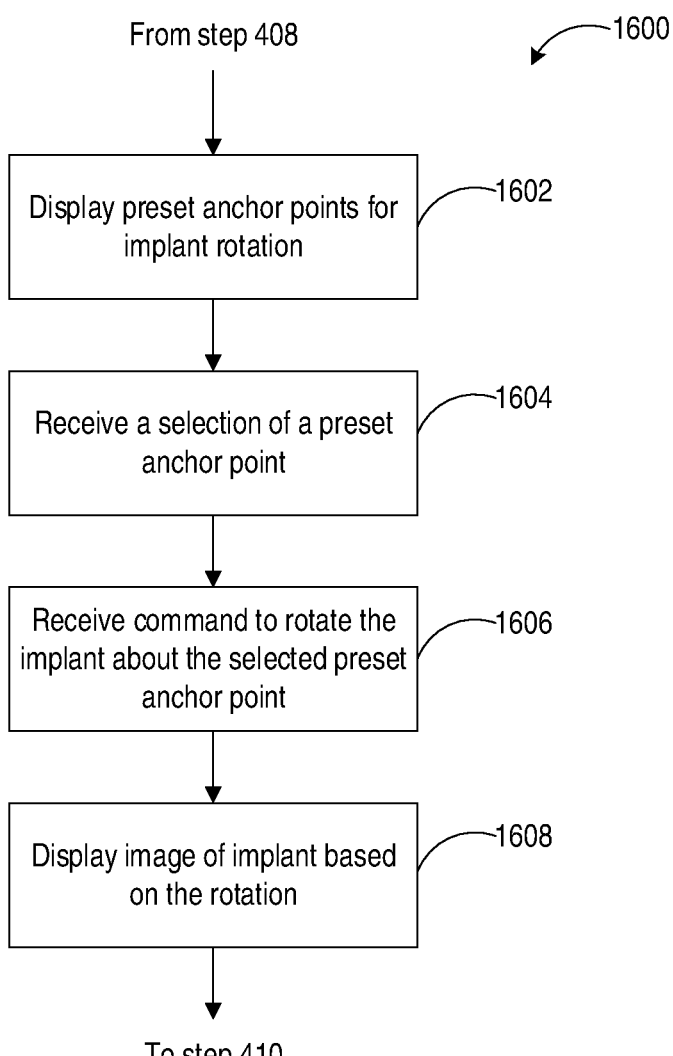
FIG. 17 is a flowchart of a process to rotate an implant about a selected anchor point, according to an exemplary embodiment.

FIG. 17 is a flowchart of a process 1600 to rotate an implant about a selected anchor point, according to an exemplary embodiment. The steps described in reference to the process 1600 can be executed by, for example, the computing system 224.

At step 1602, preset anchor points are displayed for implant rotation. For example, the computing system 224 may display to the user points on the virtual femoral implant 516 that correspond to the preset anchor points 1502-1510. The computing system 224 may also display to the user the keys associated with the present anchor points 1502-1510.

At step 1604, a selection of a preset anchor point is received. For example, the user may determine that rotation around the first preset anchor point 1502 is desired. The user then presses the key associated with the preset anchor point 1502 (e.g., the key "F1") to allow the user to manipulate the virtual femoral implant 516. In some embodiments, the user may manipulate an indicator (e.g., a cursor, a crosshair, an arrow, etc.) on the display 246 using a mouse. When the indicator is placed close to the anchor point 1502, the indicator automatically snaps to the anchor point 1502 such that the indicator is co-located with the anchor point 1502.

In another embodiment, the user may view the preset anchor points 1502-1510 in an alternate view (e.g., a CT view). When the user selects the anchor point 1502 in the CT view (either by selecting the "F1" key or by manipulating the indicator), the CT view automatically updates to show a cross-section directly through the anchor point 1502.

At step 1606, a command is received to rotate the implant about the selected preset anchor point. For example, the computing system 224 receives commands from the input/output device 262 that correspond to the desired movement of the virtual femoral implant 516. The user may provide the desired movement to the computing system 224 via the keyboard 266 (e.g., via the arrow keys, etc.) or a mouse.

At step 1608, an image of the implant is displayed based on the rotation. For example, as the user moves the virtual femoral implant using the input/output device 262, the computing system 224 shows the user the corresponding movement of the virtual femoral implant 516 on the display 246. The user can then determine, based on the view of the movement of the virtual femoral implant provided by the computing system 224, when to stop manipulating the virtual femoral implant 516. The surgical planning process can then continue.

Figure 18:
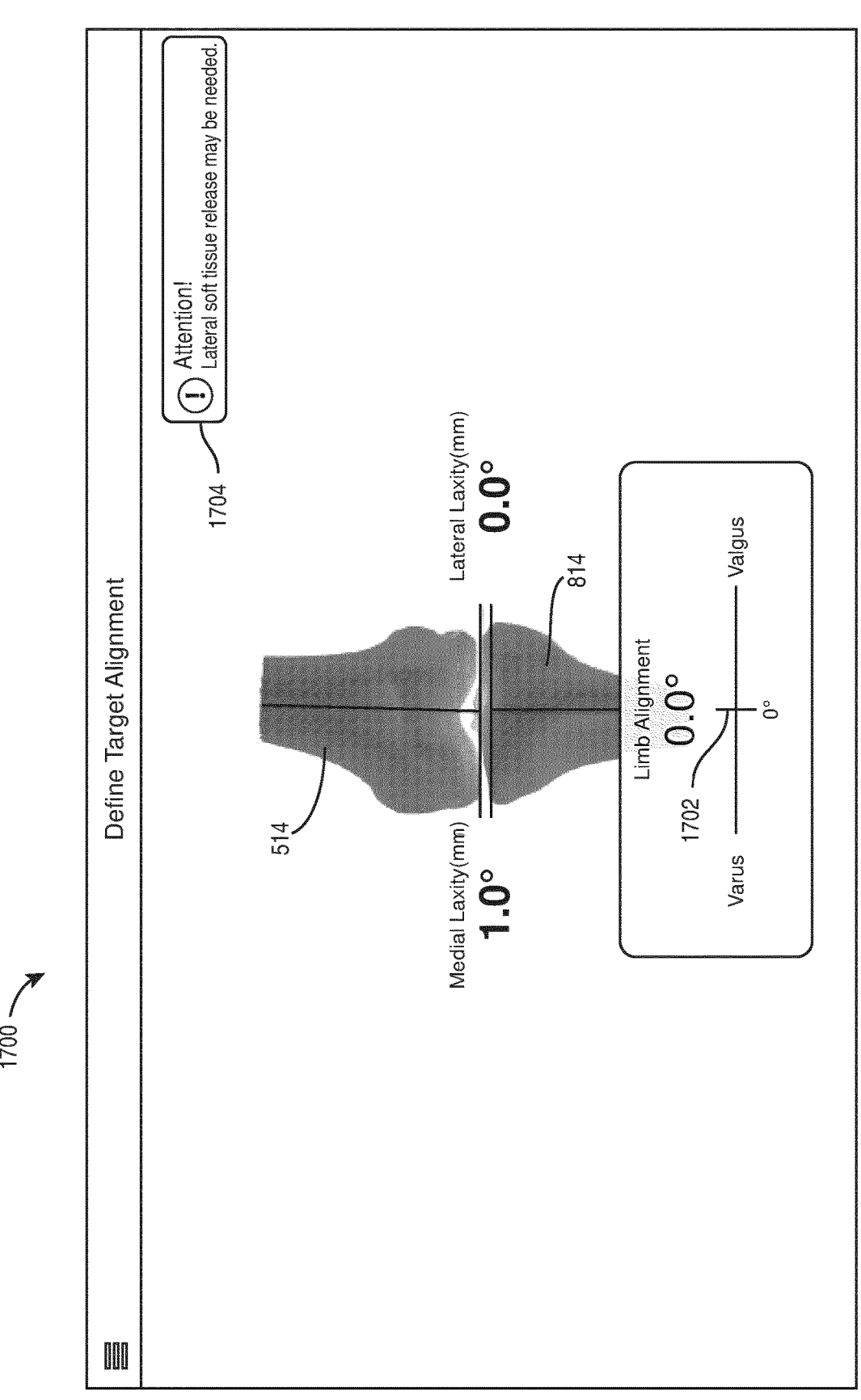
FIG. 18 is an illustration of an alignment interface, according to an exemplary embodiment.

FIG. 18 is an illustration of an alignment interface 1700, according to an exemplary embodiment. The alignment interface 1700 (e.g., "the interface 1700") may be used in conjunction with the interface described with reference to FIGS. 9-12 and FIG. 14 and/or with methods described with reference to FIGS. 15 and 17. The interface 1700 provides the user the ability to input a preference range related to alignment of the virtual femur 514 and the virtual tibia 814. To input the preference range, the user can manipulate the input/output device 266 to move a slider bar 1702 toward a varus alignment or a valgus alignment. As the user moves the slider bar 1702 in one direction or another, the computing system 224 determines whether an issue will arise during the surgical procedure based on the alignment value. If the computing system 224 determines that an issue will arise, the computing system 224 displays a warning 1704 on the interface 1700. The computing system also displays a recommended mitigation. For example, in the configuration shown in FIG. 18, the computing system has determined that, because there is zero mm of lateral laxity, the lateral soft tissue may need to be released for a successful procedure. In some embodiments, in addition to displaying the warning 1704 on the interface 1700, the number associated with the warning (e.g., the lateral laxity in the embodiment described) may be highlighted, bolded, may flash or otherwise be emphasized to draw the attention of the user. In another embodiment, the slider bar 1702 may provide the ability to define an alignment range. For example, the user may move a first slider bar 1702 a certain amount to the left, and the alignment interface 1700 may then provide a second slider bar 1702 that the user can move to the right such that the alignment range is defined by the boundaries set by the first and second slider bars.

Figure 19:
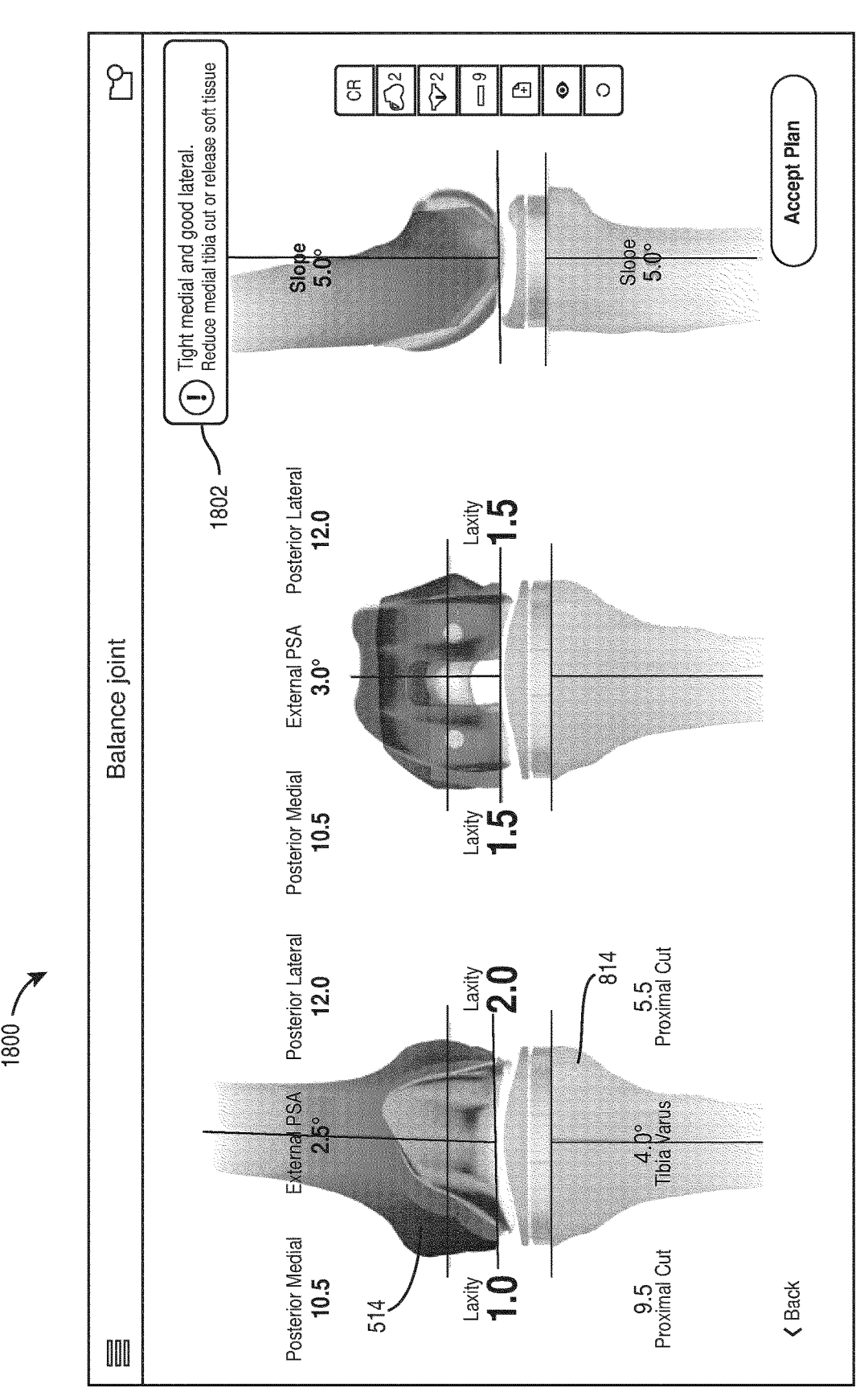
FIG. 19 is an illustration of a joint balancing interface, according to an exemplary embodiment.

FIG. 19 is an illustration of a joint balancing interface 1800, according to an exemplary embodiment. The joint balancing interface 1800 (e.g., "the interface 1800") may be used in conjunction with the interface described with reference to FIGS. 9-12 and FIG. 14 and/or with methods described with reference to FIGS. 15 and 17. The interface 1800 provides the user the ability to view how the joint between the virtual femur 514 and the virtual tibia 814 is balanced based on the planned surgical procedure. The computing system 224 analyzed the balance based on the planned surgical procedure and determines whether there is an issue with the balance of the joint. Upon determining that there is an issue with the balance of the joint, the computing system 224 displays a warning 1802 on the interface 1800 providing the reason for the warning (e.g., "tight medial"). The computing system 224 also displays a recommended mitigation (e.g., "reduce medial tibia cut or release soft tissue") to address the warning to ensure a successful procedure. In some embodiments, in addition to displaying the warning 1802 on the interface 1800, the number(s) and/or areas(s) associated with the warning (e.g., the medial tightness in the embodiment described) may be highlighted, bolded, may flash or otherwise be emphasized to draw the attention of the user.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

What is claimed is:

1. A method for controlling a robotic system to facilitate a joint arthroplasty procedure, comprising:

planning the joint arthroplasty procedure by:

providing a graphical user interface comprising a visualization of a bone model and a planned pose for an implant relative to the bone model;

in response to determining that a value descriptive of the planned pose for the implant relative to the bone model is outside a range for the value set via a surgeon preferences page of the graphical user interface, providing a marking on the graphical user interface;

removing the marking in response to an update to the planned pose for the implant relative to the bone model, wherein the update moves the value to within the range;

providing the joint arthroplasty procedure by:

facilitating the joint arthroplasty procedure by controlling the robotic system based on the planned pose; and physically installing, during the joint arthroplasty procedure, the implant on a bone in the planned pose.

2. The method of claim 1, wherein the value descriptive of the planned pose describes a rotation of the planned pose, and wherein the range indicates acceptable amounts of rotation.

3. The method of claim 1, further comprising providing the graphical user interface with an additional marking in response to an additional value descriptive of the planned pose being outside an additional range for the additional value.

4. The method of claim 3, wherein the graphical user interface comprises an indication of the value, and wherein the marking is a box around the value.

5. The method of claim 4, further comprising providing, on the graphical user interface, text describing violation of the range by the value.

6. The method of claim 1, wherein the visualization of the planned pose comprises a graphical representation of an implant positioned relative to a bone, and receiving the update to the planned pose comprises:

automatically identifying a first rotation point based on a first landmark positioned on the graphical representation of the implant;

providing a first hotkey indicator at the first rotation point, the first hotkey indicator showing a first key to be pressed to select the first rotation point;

receiving a signal indicative of a press of the first key by the user; and allowing the user to rotate the graphical representation of the implant about the first rotation point.

7. The method of claim 6, further comprising:

automatically identifying a second rotation point based on a second landmark positioned on the graphical representation of the implant;

providing a second hotkey indicator at the second rotation point, the second hotkey indicator showing a second key to be pressed to select the second rotation point;

wherein the first hotkey indicator and the second hotkey indicator are different, and wherein the first hotkey indicator is always in the same position relative to the second hotkey indicator.

8. The method of claim 1, wherein further comprising causing the graphical user interface to provide the surgeon preferences page, the surgeon preferences page configured to allow a user to set the range and a plurality of additional ranges.

9. The method of claim 8, wherein the surgeon preferences page comprises buttons selectable to adjust numerical values defining the range and the plurality of additional ranges.

10. A system for facilitating a joint arthroplasty procedure, comprising:

a robotic device configured to perform the joint arthroplasty procedure;

a computer system in communication with the robotic device, the computer system comprising a processor and a memory device, the memory device containing instructions that, when executed by the processor, cause the processor to:

generate a graphical user interface comprising a visualization of a bone model and an implant in a planned pose relative to the bone model;

identify at least a first warning by comparing the planned pose to a plurality of criteria associated with a plurality of types of warnings;

identify a particular symbol associated with the first warning from a plurality of symbols associated with the plurality of types of warnings;

provide the particular symbol on the graphical user interface such that the particular symbol overlays the visualization of the implant at a position associated with violation of a first criteria of the plurality of criteria associated with the first warning;

receive, from the graphical user interface, an update to the planned pose, wherein the update resolves the first warning; and control the robotic device based on the update to the planned pose such that the robotic device assists completion of the joint arthroplasty procedure consistent with the update to the implant plan.

11. The system of claim 10, wherein the processor is further caused to remove the particular symbol from the graphical user interface upon determining that the update to the planned pose resolved the first warning.

12. The system of claim 10, wherein the plurality of types of warnings comprise a notching warning, an airball warning, and an overhang warning.

13. The system of claim 10, wherein the plurality of types of warnings comprise a checkpoint warning, wherein the processor is further caused to compare the planned pose to a checkpoint criterion associated with the checkpoint warning by determining a distance between a cut plane associated with the planned pose and a position of a checkpoint on the bone model.

14. The system of claim 10, wherein the instructions further cause the processor, upon selection of first text associated with the first warning via the graphical user interface, to cause the first symbol to be emphasized on the graphical user interface.

15. The system of claim 10, wherein the processor is further caused to:

automatically identify a first rotation point at a first landmark of the implant or the bone model;

provide a first hotkey indicator at the first rotation point, the first hotkey indicator showing a first key to be pressed to select the first rotation point;

receive a signal indicative of a press of the first key by the user; and allow the user to rotate the visualization of the implant about the first rotation point.

16. The system of claim 15, wherein the processor is further caused to:

automatically identify a second rotation point based on a second landmark of the implant or the bone model;

provide a second hotkey indicator at the second rotation point, the second hotkey indicator showing a second key to be pressed to select the second rotation point;

wherein the first hotkey indicator and the second hotkey indicator are different, and wherein the first hotkey indicator is always in a same position relative to the second hotkey indicator.

17. A navigation system, comprising:

a surgical instrument;

a tracking system configured to track a position of the surgical instrument; and a controller programmed to:

generate a graphical user interface comprising a visualization of an implant plan comprising a graphical representation of an implant positioned relative to a bone;

receive, from the graphical user interface, an update to the implant plan, wherein the update to the implant plan by:

automatically identifying a first rotation point based on a first landmark positioned on the graphical representation of the implant;

providing a first hotkey indicator at the first rotation point, the first hotkey indicator showing a first key to be pressed to select the first rotation point;

receiving a signal indicative of a press of the first key by the user; and allowing, in response to the signal, the user to rotate the graphical representation of the implant about the first rotation point; and facilitate a joint arthroplasty procedure by providing feedback guiding the surgical instrument to a location associated with the update to the implant plan based on the position of the surgical instrument as tracked by the tracking system.

18. The system of claim 17, wherein the implant plan comprises a planned pose for the implant, and wherein the controller is further programmed to:

provide a marking on the graphical user interface in response to determining that a value descriptive of the planned pose is outside a user-defined range for the value set via a surgeon preferences page of the graphical user interface; and remove the marking in response to the update to the planned pose moving the value to within the user-defined range.

19. The system of claim 18, wherein the value descriptive of the planned pose describes a resection depth associated with the planned pose, and wherein the range indicates maximum and minimum resection depths.

20. The system of claim 18, wherein a first the marking is associated with a box around the value as displayed on the graphical user interface.

* * * * *